United States Patent
Yang et al.

(10) Patent No.: US 7,514,223 B2
(45) Date of Patent: Apr. 7, 2009

(54) CROSS-SCREENING SYSTEM AND METHODS FOR DETECTING A MOLECULE HAVING BINDING AFFINITY FOR A TARGET MOLECULE

(75) Inventors: Jihong Yang, Foster City, CA (US); Valerie Elizabeth Quarmby, Portola Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 563 days.

(21) Appl. No.: 11/128,981

(22) Filed: May 13, 2005

(65) Prior Publication Data

US 2005/0255527 A1 Nov. 17, 2005

Related U.S. Application Data

(60) Provisional application No. 60/571,157, filed on May 15, 2004, provisional application No. 60/626,827, filed on Nov. 9, 2004.

(51) Int. Cl.
G01N 33/53 (2006.01)
(52) U.S. Cl. .................. 435/7.1; 435/7.2; 435/7.91; 435/7.92
(58) Field of Classification Search ............ 435/7.1, 435/7.2, 7.91, 7.92
See application file for complete search history.

(56) References Cited

U.S. PATENT DOCUMENTS

| | | | |
|---|---|---|---|
| 3,645,852 A | 2/1972 | Axen et al. | |
| 3,654,090 A | 4/1972 | Schuurs et al. | |
| 3,691,016 A | 9/1972 | Patel | |
| 3,720,760 A | 3/1973 | Bennich et al. | |
| 3,940,475 A | 2/1976 | Gross | |
| 3,969,287 A | 7/1976 | Jaworek et al. | |
| 4,115,535 A | 9/1978 | Giaever | |
| 4,195,128 A | 3/1980 | Hildebrand et al. | |

(Continued)

FOREIGN PATENT DOCUMENTS

EP 0 404 097 A2 12/1990

(Continued)

OTHER PUBLICATIONS

Baker et al., 2002, *Trends in Biotechnology*, 20(4):149-156 "Rapid monitoring of recombinant protein products: a comparison of current technologies".

(Continued)

*Primary Examiner*—Long V. Le
*Assistant Examiner*—Changhwa J Cheu
(74) *Attorney, Agent, or Firm*—Morrison & Foerster LLP

(57) ABSTRACT

The invention is directed to a cross-screening system and methods of the invention utilizing a combination of an immunoassay (IA) and electrochemiluminescence assay (ECLA) to identify molecules that have binding affinities for a target molecule. The cross-screening system and methods of the invention can detect molecules that have binding affinities for the target molecule below the detection limits of the individual immunoassay or ECLA. The cross-screening system and methods of the invention are useful for generating a pool of candidate analyte molecules enriched in a desired characteristic, such as low binding affinity for a target molecule. Low affinity antibodies identified by the cross-screening system and methods of the invention are useful, for example, in assessing the safety and efficacy of biological therapeutics.

28 Claims, 5 Drawing Sheets

U.S. PATENT DOCUMENTS

| | | | |
|---|---|---|---|
| 4,205,952 | A | 6/1980 | Cais |
| 4,229,537 | A | 10/1980 | Hodgins et al. |
| 4,238,195 | A | 12/1980 | Boguslaski et al. |
| 4,247,642 | A | 1/1981 | Hirohara et al. |
| 4,277,437 | A | 7/1981 | Maggio |
| 4,280,815 | A | 7/1981 | Oberhardt et al. |
| 4,293,310 | A | 10/1981 | Weber |
| 4,305,925 | A | 12/1981 | Kapmeyer et al. |
| 4,330,440 | A | 5/1982 | Ayers et al. |
| 4,376,110 | A | 3/1983 | David et al. |
| 4,378,344 | A | 3/1983 | Zahradnik et al. |
| 4,419,453 | A | 12/1983 | Dorman et al. |
| 4,459,360 | A | 7/1984 | Marinkovich |
| 4,480,042 | A | 10/1984 | Craig et al. |
| 4,514,508 | A | 4/1985 | Hirschfeld |
| 4,554,088 | A | 11/1985 | Whitehead et al. |
| 4,628,037 | A | 12/1986 | Chagnon et al. |
| 4,687,732 | A | 8/1987 | Ward et al. |
| 4,695,393 | A | 9/1987 | Whitehead et al. |
| 4,698,302 | A | 10/1987 | Whitehead et al. |
| 4,711,955 | A | 12/1987 | Ward et al. |
| 4,731,337 | A | 3/1988 | Luotola et al. |
| 4,737,456 | A | 4/1988 | Weng et al. |
| 4,745,076 | A | 5/1988 | Müller et al. |
| 4,777,145 | A | 10/1988 | Luotola et al. |
| 4,816,567 | A | 3/1989 | Cabilly et al. |
| 4,965,392 | A | 10/1990 | Fritzberg et al. |
| 5,221,605 | A | 6/1993 | Bard et al. |
| 5,238,808 | A | 8/1993 | Bard et al. |
| 5,310,687 | A | 5/1994 | Bard et al. |
| 5,527,710 | A | 6/1996 | Nacamulli et al. |
| 5,543,112 | A | 8/1996 | Ghead et al. |
| 5,591,581 | A | 1/1997 | Massey et al. |
| 5,935,779 | A | 8/1999 | Massey et al. ............ 435/6 |
| 6,054,297 | A | 4/2000 | Carter et al. |
| 6,143,574 | A | 11/2000 | Karlsson et al. |
| 6,271,041 | B1 | 8/2001 | Leland et al. |
| 6,316,607 | B1 | 11/2001 | Massey et al. |
| 6,451,225 | B1 | 9/2002 | Leland et al. |
| 6,855,508 | B2 | 2/2005 | Fei et al. |

FOREIGN PATENT DOCUMENTS

| | | |
|---|---|---|
| EP | 0 404 097 A3 | 12/1990 |
| EP | 0 404 097 B1 | 12/1990 |
| WO | WO-93/11161 A1 | 6/1993 |
| WO | WO-01/36972 A2 | 5/2001 |
| WO | WO-01/36972 A3 | 5/2001 |
| WO | WO-2005/114218 A2 | 12/2005 |
| WO | WO-2005/114218 A3 | 12/2005 |

OTHER PUBLICATIONS

PCT International Search Report dated Dec. 16, 2005.

Allen, B. et al. (2003). "FASTube Electrochemiluminescense Assay Technology," *Chem-Bio Defense*, located at <http://www.jpeocbd.osd.mil/documents/jpeocbde-zine.pdf.>, p. 10.

Ausbel, F.M. et al. eds. (2003). *Current Protocols in Molecular Biology*, Wiley & Sons, Inc.: New York, NY, pp. 1-12, (Table of Contents Only.).

Clackson, T. et al. (Aug. 15, 1991). "Making Antibody Fragments Using Phage Display Libraries," *Nature* 352(6336):624-628.

Coligan, J.E. et al. eds. (2003). *Current Protocols in Immunology*, Wiley & Sons, Inc.: New York, NY, vols. 1-5, pp. 1-11, (Table of Contents Only.).

Crooks, R.M. (Dec. 3-4, 2002). "Bio/Chemical Sensing Using Thin Film Recognition Elements," *Proceedings of the WTEC Workshop on Biosensing Research and Development in the United States*, Bethesda, MD, Dec. 3-4, 2002, pp. 57-64.

David, G.S. et al. (Feb. 26, 1974). "Protein Iodination with Solid State Lactoperoxidase," *Biochemistry* 13(5):1014-1021.

Hollinger, P. et al. (Jul. 1993). "'Diabodies': Small Bivalent and Bispecific Antibody Fragments," *Proc. Natl. Acad. Sci. USA* 90:6444-6448.

Hunter, W.M. et al. (May 5, 1962). "Preparation of Iodine-131 Labelled Human Growth Hormone of High Specific Activity," *Nature* 194(4827):495-496.

Johnstone, A. et al. eds. (1996). *Immunochemistry in Practice*, Third Edition, Blackwell Science: London, England, pp. v-x, (Table of Contents Only.).

Jones, P.T. et al. (May 29, 1986). "Replacing the Complementarity-Determining Regions in a Human Antibody with Those from a Mouse," *Nature* 321(6069):522-525.

Köhler, G. et al. (Aug. 7, 1975). "Continuous Cultures of Fused Cells Secreting Antibody of Predefined Specificity," *Nature* 256(5517):495-497.

Lowman, H.B. et al. (1991)."Monovalent Phage Display: A Method for Selecting Variant Proteins from Random Libraries," in *Methods: A Companion to Methods in Enzymology*, Abelson, J.N. et al. eds., Academic Press, Inc., 3(3):205-216.

Marks, J.D. et al. (Dec. 5, 1991). "By-Passing Immunization: Human Antibodies from V-Gene Libraries Displayed on Phage," *J. Mol. Biol.* 222(3):581-597.

Morrison, S.L. et al. (Nov. 1984). "Chimeric Human Antibody Molecules: Mouse Antigen-Binding Domains with Human Constant Region Domains," *Proc. Natl. Acad. Sci. USA* 81:6851-6855.

Nygren, H. (1982). "Conjugation of Horseradish Peroxidase to Fab Fragments with Different Homobifunctional and Heterobifunctional Cross-Linking Reagents," *J. of Histochem. And Cytochem.* 30(5):407-412.

Ohlin, M. et al. (Jan. 1997). "Cytomegalovirus Glycoprotein B-Specific Antibody Analysis Using Electrochemiluminescence Detection-Based Techniques," *Clinical and Diagnostic Laboratory Immunology* 4(1):107-111.

O'Sullivan, M.J. et al. (1981). "Methods for the Preparation of Enzyme-Antibody Conjugates for Use in Enzyme Immunoassay," Chapter 9, in *Methods in Enzymology*, Langone, J.J. et al. eds., Academic Press, Inc.: New York, NY, 73(Pt. B):147-166.

Pain, D. et al. (1981). "Preparation of Protein A-Peroxidase Monoconjugate Using a Heterobifunctional Reagent, and Its Use in Enzyme Immunoassays," *J. Immunol. Methods* 40(2):219-230.

Plückthun, A. (1994). "Antibodies from *Escherichia coli*," Chapter 11 in *Handbook of Experimental Pharmacology*, Born, G.V.R et al. eds., Springer-Verlag: Hiedelberg, Germany, 113:269-315.

Presta, L.G. et al. (1992). "Antibody Engineering," *Curr. Op. Struct. Biol.* 2(4):593-596.

Reichmann, L. et al. (Mar. 24, 1998). "Reshaping Human Antibodies for Therapy," *Nature* 332(6162):323-327.

Rotmans, J.P. et al. (Feb. 25, 1983). "Cross-Linking of *Schistosoma mansoni* Antigens and Their Covalent Binding on the Surface of Polystyrene Microtitration Trays for Use in the ELISA," *J. Immunol. Methods* 57(1-3):87-98.

Wells, J.A. et al. (Aug. 1992). "Rapid Evolution of Peptide and Protein Binding Properties in vitro," *Curr. Opin. Struct. Biol.* 3(4):335-362.

Wilbur, J.L. (Dec. 3-4, 2002). "Electrochemiluminescence Based Micro-Array Systems for Biochemical Assays and Detection of Biological Agents," *Proceedings of the WTEC Workshop on Biosensing Research and Development in the United States*, Bethesda, MD, Dec. 3, 2002, pp. 40-56.

Zapata, G. et al. (Oct. 1995). "Engineering Linear F(ab')$_2$ Fragments for Efficient Production in *Escherichia coli* and Enhanced Antiproliferative Activity," *Protein Eng.* 8(10):1057-1062.

CROSS-SCREENING SYSTEM AND METHODS FOR DETECTING A MOLECULE HAVING BINDING AFFINITY FOR A TARGET MOLECULE

This application claims priority to U.S. Application Ser. No. 60/571,157, filed on May 15, 2004, and U.S. Application Ser. No. 60/626,827, filed on Nov. 9, 2004, the contents of which are hereby expressly incorporated by reference.

BACKGROUND OF THE INVENTION

Low affinity antibodies are valuable for therapeutic use, such as combination therapies. Low affinity antibodies are also useful in drug discovery. For example, where high affinity antibodies are difficult to obtain for a specific therapeutic molecule, low affinity antibodies can serve as a starting point for developing useful affinity-matured antibodies.

Anti-therapeutic molecule antibody assays, needed for regulatory approval of therapeutic molecules, require low affinity antibodies. Such assays require sensitive and efficient means to detect unwanted immune responses, important for assessing safety and efficacy of a therapeutic molecule.

Anti-therapeutic molecule antibodies can target different regions of the therapeutic and can exhibit differing binding affinities and isotypes. A panel of varied anti-therapeutic molecule antibodies mimicking the polyclonal nature of an immune response is desirable, to more accurately assess performance of anti-therapeutic molecule antibody assays.

Screening hybridoma clones for high affinity antibodies has traditionally utilized ELISA technology. ELISA, however, is not as effective for screening low affinity antibodies. Although ELISA can identify antibodies that bind an antigen, the assay cannot readily identify antibodies that bind with low affinity. Many low affinity antibodies are lost in the multiple wash steps required to ensure a high signal-to-noise ratio. Minimizing wash steps to retain these low affinity antibodies, however, decreases sensitivity of the assay by decreasing the signal-to-noise ratio.

A minimal number of wash steps are required in electrochemiluminescence assay (ECLA), permitting the ECLA system to detect low affinity antibodies that would be washed away by traditional ELISA methods. Simply replacing ELISA with ECLA is not a good solution, however. Like ELISA, ECLA cannot readily identify antibodies that bind with low affinity. In addition, labeling agents used in ECLA have the potential to alter binding properties of the antibodies. ECLA can thus fail to retain antibodies that would otherwise be retained by conventional ELISA methods.

Efficient assay systems and methods are greatly needed for screening a pool of analyte molecules, such as antibodies, to identify those having specific characteristics, including low affinity antibodies, anti-therapeutic molecule antibodies responsive to a variety of epitopes, and the like. In particular, efficient and reliable methods to identify a pool of analyte molecules enriched with those having a desired affinity (low or high) or likely to contain analyte molecules responsive to differing binding sites of a target molecule, would be very useful.

SUMMARY OF THE INVENTION

The present invention provides a cross-screening system and methods for crossing an immunoassay with ECLA to identify analyte molecules, such as antibodies, that have selective binding affinity for a target molecule. Analyte molecules are identified as having a particular characteristic, such as low or high binding affinity and/or binding to differing binding sites of a target molecule. The cross-screening system and methods of the invention detect analyte molecules that are below the detection limits of an immunoassay (IA) or ECLA individually. Binding to a target molecule is assayed in both immunoassay methods, such as ELISA, and in ECLA.

A cross-screening system and methods of the invention generally employ the following steps: (1) determining ECLA responses for individual members of a pool of analyte molecules binding to a target molecule; (2) determining IA responses for individual members of the pool of analyte molecules binding the target molecule; and (3) generating a pool of candidate analyte molecules enriched in a desired characteristic, such as low or high binding affinity or variety of the antigenic epitopes.

Data from a large pool of analyte molecules is produced and evaluated as $IA^+$ or $IA^-$; $ECLA^+$ or $ECLA^-$. Molecules that are $IA^+/ECLA^+$, $IA^-/ECLA^+$, or $IA^+/ECLA^-$ are identified as analyte molecules that specifically bind the target molecule.

The candidate analyte molecule is selected from an enriched pool of analyte molecules generated on the basis of the respective ECLA and IA responses, for example, $IA^-/ECLA^-$, $IA^+/ECLA^-$, $IA^-/ECLA^+$, or $IA^+/ECLA^+$. Analyte molecules and/or target molecules can be antibodies. In one embodiment, the target molecules are therapeutic antibodies and the analyte molecules are anti-therapeutic antibodies.

In an embodiment, IA and ECLA responses are determined within detection limits of the respective assays. An ECLA response equal to or greater than the ECLA detection limit is $ECLA^+$. An ECLA response less than the ECLA detection limit is $ECLA^-$. An IA response equal to or greater than the IA detection limit is $IA^+$. An IA response less than the IA detection limit is $IA^-$. A candidate low affinity analyte molecule is $IA^-/ECLA^+$. A candidate high affinity analyte molecule is $IA^+/ECLA^+$ or $IA^+/ECLA^-$. Analyte molecules that are $IA^+/ECLA^-$ include candidate analyte molecules that bind a target molecule at a binding site that is masked or altered in the ECLA assay, for example, by biotin or a chemical label employed in ECLA.

The cross-screening system and methods of the invention optionally include confirming specific binding affinity of a candidate analyte molecule, for example, by surface plasmon resonance analysis such as Biacore, competitive ELISA, equilibrium dialysis, radioimmunoassay, and the like. Candidate low affinity analyte molecules demonstrating a $K_{dissoc}$ greater than $10^{-6}$ 1/sec or a $K_D$ equal to or greater than $10^{-8}$ M, for example, can be confirmed as low affinity antibodies. Low affinity analyte molecules identified by the cross-screening system and methods of the invention generally demonstrate a $K_{dissoc}$ equal to or greater than about $10^{-5}$ 1/sec or a $K_D$ of about $10^{-6}$ M to about $10^{-8}$ M.

The cross-screening system and methods of the invention optionally include confirming the isotype of a candidate analyte molecule that is an antibody, for example, by isotyping ELISA.

The cross-screening system and methods of the invention can also be used to detect small amounts of an analyte in a sample. For example, the cross-screening system and methods of the invention can be used to identify a hybridoma producing a low concentration of antibodies that have affinity for the target molecule. The concentration of antibody in the supernatant can be below the detection limit of the individual immunoassay or ECLA, but not the detection limit of the cross-screening system and methods of the invention, for example, ($ECLA^-/IA^+$ or $ECLA^+/IA^-$).

The cross-screening system and methods are useful to screen analyte molecules such as small molecules, polypeptides, or polypeptide fragments. The system and methods are particularly useful to screen antibodies, soluble receptors, or fragments thereof. The antibodies can be monoclonal. In an embodiment, the antibodies are monoclonal anti-therapeutic molecule antibodies.

The target molecule is typically a small molecule, polypeptide, or polypeptide fragment. The target molecule can be, for example, an antigen if the analyte is an antibody, a receptor or antibody if the analyte is a small molecule or polypeptide, a polypeptide or small molecule if the analyte is a soluble receptor, or phage expressing antibodies, soluble receptors, or fragments thereof if the analyte is a polypeptide or small molecule. The target molecule can be a polypeptide or antibody having therapeutic activity. When the target molecule is a therapeutic antibody or therapeutic polypeptide, the cross-screening system and method can identify low affinity analyte antibodies.

The cross-screening system and methods of the invention have many uses. The system and methods of the invention can be used to screen serum from a patient who is about to receive or is receiving a therapeutic molecule for antibodies to the therapeutic molecule. The system and methods of the invention can be used to screen libraries of receptors, antibodies, polypeptides, small molecules, and the like, for library members that bind a target molecule with specific binding characteristics.

Low affinity antibodies identified by the cross-screening system and methods of the invention are particularly useful in anti-therapeutic molecule assays for evaluating the efficacy and safety of therapeutic molecules in clinical trials. Low affinity antibodies identified by the cross-screening system and methods of the invention can also serve as a starting point for developing affinity-matured antibodies.

DETAILED DESCRIPTION OF THE PREFERRED EMBODIMENTS

I. Definitions

Figure 1:
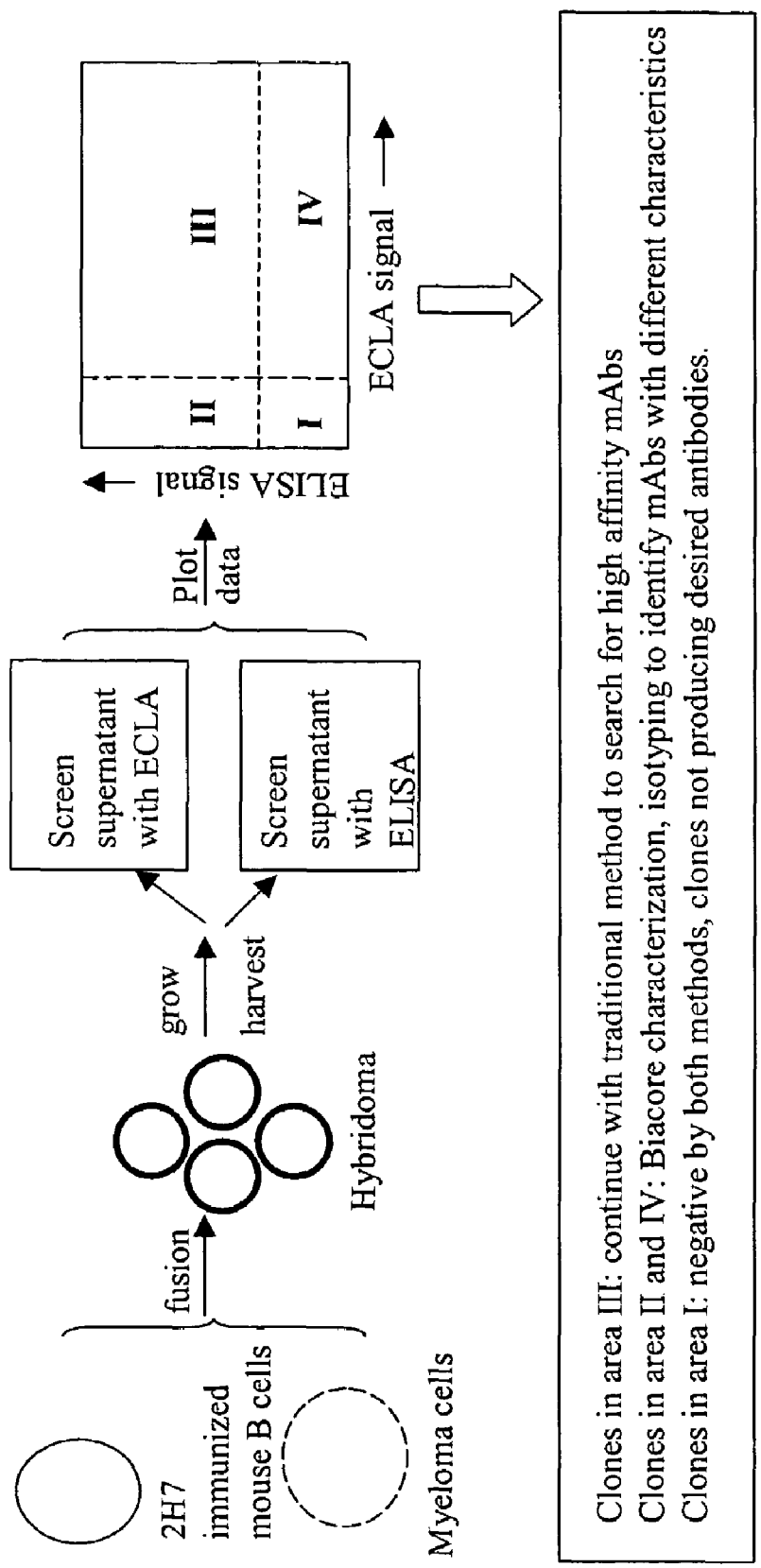
FIG. 1 is a workflow diagram showing an embodiment of the cross-screening system and methods of the invention applied to identify low affinity antibodies for a specific antigen.

As used herein, the term "Immunoassay" (IA) means a serological assay in which bound analyte is detected by a labeled moiety linked to a detecting agent. Immunoassay includes, but is not limited to, radioimmunoassay (RIA), fluoroluminescence assay (FLA), chemiluminescence assay (CLA), and enzyme-linked immunosorbant assay (ELISA). ELISA methods are described, for example, in WO01/36972. Immunoassays are useful for detecting the presence of analyte molecules, such as antibodies, that bind target molecules, such as antigens.

The term "detecting" is used in the broadest sense to include both qualitative and quantitative measurements of a specific molecule, herein measurements of a specific analyte molecule such as an anti-therapeutic antibody. In one aspect, a detection method as described herein is used to identify the mere presence of an analyte molecule of interest in a sample. In another aspect, the method can be used to quantify an amount of analyte molecule in a sample. In still another aspect, the method can be used to determine the relative binding affinity of an analyte molecule of interest for a target molecule.

The term "detecting agent" refers to an agent that detects an analyte molecule, either directly via a label, such as a fluorescent, enzymatic, radioactive, or chemiluminescent label, that can be linked to the detecting agent, or indirectly via a labeled binding partner, such as an antibody or receptor that specifically binds the detecting agent. Examples of detecting agents include, but are not limited to, an antibody, antibody fragment, soluble receptor, receptor fragment, and the like. In an embodiment, the detecting agent can be expressed on a phage.

The term "label" includes agents that amplify a signal produced by a detecting agent. The label can be a radiologic, photoluminescent, chemiluminescent, or electrochemiluminescent chemical moiety, an enzyme that converts a colorless substrate into a colored product, and the like.

The term "capture reagent" refers to a reagent capable of binding and capturing a target molecule or analyte molecule in a sample. Typically, a capture reagent is immobilized, for example, on a solid substrate, such as a microparticle or bead, microtiter plate, column resin, and the like. The capture reagent can be an antigen, soluble receptor, antibody, a mixture of different antibodies, and the like.

The term "target molecule" refers to a specific binding target of an analyte molecule identified by the cross-screening system and methods of the invention. A target molecule is typically a small molecule, polypeptide, or polypeptide fragment. The target molecule can be, for example, an antigen if the analyte molecule is an antibody, a receptor or antibody if the analyte molecule is a small molecule or polypeptide, a polypeptide or small molecule if the analyte molecule is a soluble receptor, a phage expressing antibody, soluble receptor, or fragments thereof if the analyte molecule is a polypeptide or small molecule. The target molecule can be, for example, a polypeptide or antibody having therapeutic activity. In one embodiment, the target molecule is a therapeutic antibody and the analyte molecule is an anti-therapeutic antibody that binds the therapeutic antibody.

"Analyte" and "analyte molecule," as used herein, refer to a molecule that is analyzed by the cross-screening system and methods of the invention, and includes, but is not limited to, small molecules, polypeptides, polypeptide fragments, antibodies, antibody fragments, phage, displayed polypeptides, and the like. In the cross-screening system and methods of the invention, an analyte molecule has a binding affinity for the target molecule.

"Polypeptide" refers to a peptide or protein containing two or more amino acids linked by peptide bonds, and includes peptides, oligomers, proteins, and the like. Polypeptides can contain natural, modified, or synthetic amino acids. Polypeptides can also be modified naturally, such as by post-translational processing, or chemically, such as amidation acylation, cross-linking, and the like.

As used herein, an "anti-therapeutic antibody" is an antibody that binds a therapeutic antibody. For example, anti-2H7 antibody is an antibody that binds 2H7, a therapeutic antibody.

"Low affinity", as used herein, means an analyte molecule having a dissociation rate constant ($K_{dissoc}$) generally greater then $10^{-6}$ 1/sec for a target molecule. Preferably the $K_{dissoc}$ of the analyte molecule for the target molecule is $10^{-5}$ 1/sec or greater, $10^{-4}$ 1/sec or greater, $10^{-3}$ 1/sec or greater, or $10^{-2}$ 1/sec or greater. Useful low affinity antibodies typically have a dissociation rate constant of about $10^{-3}$ to $10^{-5}$ 1/sec. A molecule with a high dissociation rate constant ($K_{dissoc}$) is likely to have low affinity, as the equilibrium dissociation constant, $K_D = K_{dissoc}/K_{assoc}$. A molecule with an equilibrium constant ($K_D$) equal to or greater than about $10^{-8}$ M has low binding affinity. Useful low affinity antibodies can have a $K_D$ of about $10^{-6}$ M to about $10^{-8}$ M, for example.

Electrochemiluminescence assay or "ECLA" is an electrochemical assay in which bound analyte molecule is detected by a label linked to a detecting agent (target molecule). An electrode electrochemically initiates luminescence of a chemical label linked to a detecting agent. Light emitted by the label is measured by a photodetector and indicates the presence or quantity of bound analyte molecule/target molecule complexes. ECLA methods are described, for example, in U.S. Pat. Nos. 5,543,112; 5,935,779; and 6,316,607. Signal modulation can be maximized for different analyte molecule concentrations for precise and sensitive measurements.

Microparticles can be suspended in the IA or ECLA sample to concentrate the analyte. For example, the particles can have a diameter of 0.05 μm to 200 μm, 0.1 μm to 100 μm, or 0.5 μm to 10 μm, and a surface component capable of binding an analyte molecule. In an embodiment, the microparticles have a diameter of about 3 μm. The microparticles can be formed of crosslinked starch, dextran, cellulose, protein, organic polymers, styrene copolymer such as styrene/butadiene copolymer, acrylonitrile/butadiene/styrene copolymer, vinylacetyl acrylate copolymer, vinyl chloride/acrylate copolymer, inert inorganic particles, chromium dioxide, oxides of iron, silica, silica mixtures, proteinaceous matter, or mixtures thereof, including but not limited to sepharose beads, latex beads, shell-core particles, and the like. The microparticles are preferably monodisperse, and can be magnetic, such as paramagnetic beads. See, for example, U.S. Pat. Nos. 4,628,037; 4,965,392; 4,695,393; 4,698,302; and 4,554,088. Microparticles can be used in an amount ranging from about 1 to 10,000 μg/ml, preferably 5 to 1,000 μg/ml.

A "detection limit" for an analyte molecule in a particular assay is a minimum concentration of the analyte molecule that can be detected above background levels for that assay. For example, in IA and ECLA, the detection limit for an analyte molecule that specifically binds a target molecule can be the concentration at which the analyte molecule produces an IA signal or ECLA signal above that produced by a control antibody that does not bind, or non-specifically binds, the target antigen. Molecules that have an IA response less than the IA detection limit are $IA^-$. Molecules that have an IA response equal to or greater than the IA detection limit are $IA^+$. Molecules that have an ECLA response less than the ECLA detection limit are $ECLA^-$. Molecules that have an ECLA response equal to or greater than the ECLA detection limit are $ECLA^+$. Detection limits can be raised or lowered to achieve a desired assay result.

The term "antibody" is used in the broadest sense and specifically includes single monoclonal antibodies (including agonist and antagonist antibodies), antibody compositions with polyepitopic specificity, affinity-matured antibodies, humanized antibodies, chimeric antibodies, single chain antigen binding molecules such as monobodies, as well as antigen binding fragments or polypeptides (e.g., Fab, $F(ab')_2$, scFv, and Fv) that exhibit a desired biological activity. An antibody can be natural or synthetic.

"Natural" or "naturally occurring" antibodies are derived from a nonsynthetic source, for example, from a differentiated antigen-specific B cell obtained ex vivo, or its corresponding hybridoma cell line, or from the serum of an animal. These include antibodies generated in any type of immune response, either natural or otherwise induced. As used herein, natural antibodies differ from "synthetic antibodies", synthetic antibodies referring to antibody sequences that have been changed, for example, by the replacement, deletion, or addition of one or more amino acid, resulting in an antibody sequence that differs from the source antibody sequence.

The term "monoclonal antibody" as used herein refers to a natural or synthetic antibody obtained from a population of substantially homogeneous antibodies, i.e., the individual antibodies comprising the population are identical except for possible naturally-occurring mutations that can be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., 1975, *Nature*, 256: 495, or can be made by recombinant DNA methods (see, e.g., U.S. Pat. No. 4,816,567). The monoclonal antibodies can also be isolated from phage antibody libraries using the techniques described in Clackson et al., 1991, *Nature*, 352:624-628 (1991) and Marks et al., 1991, *J. Mol. Biol.*, 222:581-597, for example.

The term monoclonal antibodies specifically includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a desired biological activity (U.S. Pat. No. 4,816,567; and Morrison et al., 1984, *Proc. Natl. Acad. Sci. USA*, 81:6851-6855).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, specific framework region (FR) residues of the human immunoglobulin can be replaced by corresponding non-human residues. Furthermore, humanized antibodies can comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable regions correspond to those of a non-human immunoglobulin and all or substantially all of the FRs correspond to those of a human immunoglobulin sequence. The humanized antibody optionally also will comprise at least a portion of an immunoglobulin constant region (Fc), typically that of a human immunoglobulin. For further details, see Jones et al., 1986, *Nature*, 321:522-525; Reichmann et al., 1998, *Nature*, 332: 323-329; and Presta et al., 1992, *Curr. Op. Struct. Biol.*, 2:593-596. Heavy and light chain variable domains of a humanized antibody can also contain consensus framework regions as described, for example, in U.S. Pat. No. 6,054,297 to Carter.

An "Fv" fragment is an antibody fragment that contains a complete antigen recognition and binding site. This antibody fragment comprises a dimer of one heavy and one light chain variable domain in tight association that can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (comprising only three CDRs specific for an antigen) has the ability to recognize and bind antigen.

A "Fab" fragment contains a variable and constant domain of the light chain and a variable domain and the first constant domain (CH1) of the heavy chain. F(ab)'$_2$ antibody fragments comprise a pair of Fab fragments that are generally covalently linked near their carboxy termini by hinge cysteines. Other chemical couplings of antibody fragments are also known.

"Single-chain Fv" or "scFv" antibody fragments comprise the $V_H$ and $V_L$ domains of antibody, where these domains are present in a single polypeptide chain. Generally the Fv polypeptide further comprises a polypeptide linker between the $V_H$ and $V_L$ domains that enables the scFv to form the desired structure for antigen binding. For a review of scFv, see Pluckthun, 1994, In: *The Pharmacology of Monoclonal Antibodies*, Vol. 113, Rosenburg and Moore eds. Springer-Verlag, New York, pp. 269-315.

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993, *Proc. Natl. Acad. Sci. USA*, 90:6444-6448.

The expression "linear antibodies" refers to antibodies as described in Zapata et al., 1995, *Protein Eng.*, 8(10):1057-1062. Briefly, these antibodies contain a pair of tandem Fd segments ($V_H$-$C_H$1-$V_H$-$C_H$1) that, together with complementary light chain polypeptides, form a pair of antigen binding regions. Linear antibodies can be bispecific or monospecific.

The term "monobody" as used herein, refers to an antigen binding molecule with a heavy chain variable domain and no light chain variable domain. A monobody can bind to an antigen in the absence of light chains and typically has three CDR regions designated CDRH1, CDRH2, and CDRH3. A heavy chain IgG monobody has two heavy chain antigen binding molecules connected by a disulfide bond. The heavy chain variable domain comprises one or more CDR regions, preferably a CDRH3 region. A "$V_h$H" or "VHH" refers to a variable domain of a heavy chain antibody such as a monobody.

"Enriching" a pool of analyte molecules, as used herein, refers to analytical means for generating a pool of analyte molecules that possess a desired characteristic from a larger pool of analyte molecules. By viewing the cross-screening affinity data according to the system and methods of the invention, analyte molecules lacking the desired characteristic are eliminated, resulting in a pool of analyte molecules enriched for analyte molecules having the desired characteristic. For example, by viewing the cross-screening affinity data obtained from ELISA and ECLA analysis of a pool of candidate anti-therapeutic antibodies as described in the Examples below, antibodies that demonstrate an ELISA$^-$/ECLA$^+$ response form a pool of candidate antibodies enriched for candidate low affinity anti-therapeutic antibodies.

The term "library" refers to a plurality of polypeptide or polypeptide fragment sequences, the sequences being different in the combination of variant amino acids that are introduced into these sequences. In one embodiment, the polypeptide or polypeptide fragment sequences are antibody or antibody fragment sequences.

"Phage display" is a technique by which variant polypeptides are displayed as fusion proteins to a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phages has been used for screening millions of polypeptides for ones with specific binding properties. Polyvalent phage display methods have been used for displaying small random peptides and small proteins through fusions to either gene III or gene VIII of filamentous phage. Wells and Lowman, 1992, *Curr. Opin. Struct. Biol.*, 3:355-362, and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity. Lowman and Wells, 1991, *Methods: A Companion to Methods in Enzymology*, 3:205-0216.

2H7, also known as PRO70769, refers to a humanized monoclonal antibody that binds human CD20 antigen expressed on most B cells. 2H7 is currently being evaluated in clinical phase I/II trails for treatment of rheumatoid arthritis. Monoclonal antibody 2H7 is commercially available, for example, from eBioscience, San Diego, Calif.

Bevacizumab refers to a humanized monoclonal anti-VEGF antibody that inhibits angiogenesis. Bevacizumab is approved for treatment of metastatic cancer of the colon or rectum and is currently being evaluated in clinical phase III trials for treatment of other types of cancers including pancreatic, renal, and breast cancers. Bevacizumab is commercially available from Genentech Inc., South San Francisco, Calif.

II. Methods for Carrying Out the Invention

The invention provides a cross-screening system and methods that analyze data generated in immunoassay (IA) and electrochemiluminescent assay (ECLA) methods to identify analyte molecules that have binding affinity for a target molecule. The cross-screening system and methods of the invention identify analyte molecules having binding affinities for a target molecule that are below detection limits of the individual immunoassay or ECLA.

In one aspect of the invention, the binding affinity of analyte molecules for a target molecule is cross-screened using immunoassay and ECLA methods. Analyte molecules that are IA$^+$/ECLA$^+$, IA$^-$/ECLA$^+$, or IA$^+$/ECLA$^-$ are identified as analyte molecules that specifically bind the target molecule.

As shown in FIG. 1, a pool of analyte molecules enriched for analyte molecules having a particular binding affinity for a target molecule can be generated from a large pool of analyte molecules using an embodiment of the cross-screening system and methods of the invention. The large pool of analyte molecules is screened with IA and ECLA. Optionally, the IA signal of the individual analyte molecules in the pool is plotted against the respective ECLA signal (FIG. 1). Analyte molecules in areas II (IA$^+$/ECLA$^-$) and III (IA$^+$/ECLA$^+$) form an enriched pool of candidate high affinity molecules (FIG. 1). Analyte molecules in area IV (IA$^-$/ECLA$^+$) form an enriched pool of candidate low affinity analyte molecules (FIG. 1). Analyte molecules from the enriched pools of candidate low or high affinity analyte molecules can be confirmed as low or high affinity molecules by determining the specific binding affinity of a selected analyte molecule, for example by surface plasmon resonance analysis. If the analyte molecules are monoclonal antibodies, the antibodies can be isotyped to identify monoclonal antibodies with different characteristics.

Analyte molecules that can be screened by the system and methods of the invention are typically small molecules, polypeptides, or polypeptide fragments, and can be, for example, antibodies, soluble receptors, or fragments thereof. Antibodies can be monoclonal antibodies, typically produced by hybridoma cells. Polypeptides, such as antibodies, soluble receptors, and fragments thereof, can also be expressed on phage. Therefore, a pool of analyte molecules can be a phage library.

A target molecule useful in the system and methods of the invention, is typically a small molecule, polypeptide, or polypeptide fragment. The target molecule can be, for example, an antigen if the analyte is an antibody, a receptor or antibody if the analyte is a small molecule or polypeptide, a polypeptide or small molecule if the analyte is a soluble receptor, or a phage expressing antibodies, soluble receptors, or fragments thereof if the analyte is a polypeptide or small molecule.

Preferably the target molecule is an antigen, and can be, for example, a polypeptide, polypeptide fragment, or small molecule. Examples of target molecules include, but are not limited to, renin; growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); serum albumin such as human serum albumin; Muellerian-inhibiting substance; relaxin A-chain; relaxin B-chain; prorelaxin; mouse gonadotropin-associated peptide; microbial protein, such as beta-lactamase; DNase; IgE; cytotoxic T-lymphocyte associated antigen (CTLA), such as CTLA-4; inhibin; activin; vascular endothelial growth factor (VEGF); EG-VEGF; Bv8; receptors for hormones or growth factors; protein A or D; rheumatoid factors; neurotrophic factor such as bone-derived neurotrophic factor (BDNF), neurotrophin-3, -4, -5, or -6 (NT-3, NT-4, NT-5, or NT-6), or nerve growth factor; platelet-derived growth factor (PDGF); fibroblast growth factor such as aFGF and bFGF; epidermal growth factor (EGF); transforming growth factor (TGF) such as TGF-alpha and TGF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; tumor associated antigen such as HER2, HER3, or HER4 receptor; fragments of any of the above-listed polypeptides or specific epitopes thereof; and antibodies that bind any of these polypeptides.

Preferred target molecules for screening antibody analyte molecules include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150,95, VLA-4, ICAM-1, VCAM and $\alpha_v\beta_3$ integrin including either alpha or beta subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; and antibodies that bind any of these polypeptides.

A target molecule can also be a polypeptide or antibody having therapeutic properties or activity. For example, a polypeptide that induces angiogenesis, such as for example VEGF, EG-VEGF, or Bv8, can be used therapeutically to promote healing of a wound or surgical incision in a tissue. In an embodiment, the target molecule is an antigen, such as and anti-therapeutic monoclonal antibody. Examples of anti-therapeutic monoclonal antibodies useful as target molecules in the invention include, but are not limited to, anti-VEGF antibodies such as bevacizumab and LUCENTIS™, anti-HER2 antibodies such as HERCEPTIN® and OMNI-TARG™, anti-CD20 antibodies such as RITUXAN® and PRO70769, anti-IgE antibodies such as XOLAIR®, and anti-CD11a antibodies such as RAPTIVA®. In an embodiment, the target molecule is the monoclonal antibody 2H7 and the analyte molecule to be screened is a pool of anti-2H7 antibodies or hybridoma supernatants of clones producing such anti-2H7 antibodies. In an embodiment, the target molecule is the monoclonal antibody bevacizumab and the analyte molecule to be screened is a pool of anti-bevacizumab antibodies or hybridoma supernatants of clones producing such anti-bevacizumab antibodies.

When the target molecule is a therapeutic antibody or therapeutic polypeptide, the cross-screening system and methods of the invention can be used to identify enriched pools of candidate anti-therapeutic antibodies for candidate anti-therapeutic antibodies having low binding affinity for the target molecule (therapeutic antibody), as described in the Examples below.

A. Immunoassay

Conventional immunoassays can be used in the cross-screening system and methods of the invention. Examples of immunoassays useful in the invention include, but are not limited to, radioimmunoassay (RIA), fluoroluminescence assay (FLA), chemiluminescence assay (CA), and enzyme-linked immunosorbant assay (ELISA). See, for example, Johnstone and Thorpe, *Immunochemistry in Practice*, Blackwell, 3rd ed., 1996; *Current Protocols in Molecular Biology*, Ausbul et al. eds., Wiley & Sons, 2003; *Immunoassay Methods and Protocols*, Ghindilis et al. eds., Blackwell, 2003; U.S. 20030044865. The immunoassay can be a solid phase assay or liquid phase assay. Preferably the immunoassay is a solid phase assay such as, for example, ELISA.

Analyte molecules in a sample can be concentrated using microparticles. The microparticles can be polymeric, including but not limited to, sepharose beads, latex beads, and shell-core particles. See, for example, U.S. Pat. Nos. 4,305,925; 4,480,042; and 4,419,453. The microparticles can be magnetic to facilitate separation of the beads or microparticles from the sample. See, for example, U.S. Pat. Nos. 4,731,337; 4,777,145; and 4,115,535. Preferably, the magnetic beads are paramagnetic beads such as, for example, DYNABEADS (Dynal Biotech, Brown Deer, Wis.). When microparticles are used in the assay, a target molecule is conjugated to the beads. The target molecule can be conjugated to the microparticle by a non-covalent or covalent interaction or physical linkage as desired. For example, the microparticles can be coated with streptavidin to provide a binding surface for biotinylated target molecules. Techniques for attachment include those described in U.S. Pat. No. 4,376,110 and the references cited therein.

Preferably the immunoassay is a solid-phase ELISA or a capture ELISA. In a capture ELISA, immobilization of the target molecule to a solid phase is conventionally accomplished by insolubilizing a capture reagent either before the assay procedure, as by adsorption to a water-insoluble matrix or surface (U.S. Pat. No. 3,720,760) or non-covalent or covalent coupling, for example, using glutaraldehyde or carbodiimide cross-linking, with or without prior activation of the support with, for example, nitric acid and a reducing agent as described in U.S. Pat. No. 3,645,852 or in Rotmans et al., 1983, *J. Immunol. Methods,* 57:87-98, or after the assay procedure, for example, by immunoprecipitation. In an embodiment, the capture reagent is an antibody or a mixture of different antibodies against a target antigen or an antibody/antigen complex, where the bound antigen is available to bind an antibody from a sample. In a further embodiment, the capture reagent is an anti-isotype specific antibody complexed to a therapeutic antibody. For example, the capture reagent can be a goat anti-human IgG Fc specific antibody complexed to a humanized therapeutic IgG monoclonal antibody. In an embodiment, the humanized therapeutic IgG monoclonal antibody is an anti-2H7 antibody. In an embodiment, the humanized therapeutic IgG monoclonal antibody is an anti-bevacizumab antibody.

The solid phase used for immobilization can be any inert support or carrier that is essentially water insoluble and useful in immunoassays, including supports in the form of, for example, surfaces, particles, porous matrices, and the like. Examples of commonly used supports include small sheets, Sephadex, polyvinyl chloride, plastic beads, microparticles, assay plates, or test tubes manufactured from polyethylene, polypropylene, polystyrene, and the like. Such supports include 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. In an embodiment the immobilized capture reagent is coated on a microtiter plate. The preferred solid phase is a multi-well microtiter plate that can be used to analyze several samples at one time.

The solid phase is coated with the capture reagent that can be linked by a non-covalent or covalent interaction or physical linkage, as desired. Techniques for attachment include those described in U.S. Pat. No. 4,376,110 and the references cited therein. If covalent attachment of the capture reagent to the plate is utilized, the plate or other solid phase can be incubated with a cross-linking agent together with the capture reagent. Commonly used cross-linking agents for attaching the capture reagent to the solid phase substrate include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light.

If polystyrene or polypropylene plates are utilized, the wells in the plate are preferably coated with the capture reagent (typically diluted in a buffer such as 0.05 M sodium carbonate) by incubation for at least about 10 hours, more preferably at least overnight, at temperatures of about 4-20° C., more preferably about 4-8° C., and at a pH of about 8-12, more preferably about 9-10, and most preferably about 9.6. If shorter coating times (1-2 hours) are desired, the plate is coated at 37° C. or plates with nitrocellulose filter bottoms such, as for example, Millipore MULTISCREEN™. The plates can be stacked and coated in advance of the assay, allowing for an immunoassay to be carried out simultaneously on several samples in a manual, semi-automatic, or automatic fashion, such as by using robotics.

The coated plates are typically treated with a blocking agent that binds non-specifically to, and saturates, the binding sites to prevent unwanted binding of free ligand to excess binding sites on the wells of the plate. Examples of appropriate blocking agents include, for example, gelatin, bovine serum albumin, egg albumin, casein, and non-fat milk. The blocking treatment typically takes place under conditions of ambient temperatures for about 1-4 hours, preferably about 1.5 to 3 hours.

After coating and blocking, the sample to be analyzed is diluted as necessary and added to the immobilized phase. The preferred dilution rate is about 5-15%, preferably about 10%, by volume. Buffers that can be used for dilution include for example (a) phosphate buffered saline (PBS) containing 0.5% BSA, 0.05% TWEEN 20™ detergent (P20), 5 mM EDTA, 0.25% Chaps surfactant, 0.2% beta-gamma globulin, and 0.35M NaCl, pH 7.0; (b) PBS containing 0.5% BSA and 0.05% P20; (c) PBS containing 0.5% BSA, 0.05% P20, 5 mM EDTA, and 0.35 M NaCl, pH 6.35; (d) PBS containing 0.5% BSA, 0.05% P20, 5 mM EDTA, 0.2% beta-gamma globulin, and 0.35 M NaCl; (e) PBS containing 0.5% BSA, 0.05% P20, 5 mM EDTA, 0.25% Chaps, and 0.35 M NaCl; and (f) PBS containing 0.5% P20.

For sufficient sensitivity, it is preferred that the immobilized capture reagent is in molar excess of the maximum molar concentration of the analyte anticipated in the sample after appropriate dilution. Depending on the analyte, the capture reagent can compete for binding sites with the detecting antibody yielding inaccurate results. Therefore, the final concentration of the capture reagent will normally be determined empirically to maximize the sensitivity of the assay over the range of interest.

Conditions for incubation of sample and capture reagent are selected to maximize sensitivity of the assay and to minimize dissociation. Incubation time depends primarily on the temperature. Preferably, the incubation time is from about 0.5 to 3 hours, and more preferably 1.5-3 hours at 36-38° C. To maintain the sensitivity of the assay, incubation times greater than about 10 hours are avoided if possible. If the sample is a biological fluid, incubation times can be lengthened by adding a protease inhibitor to the sample to prevent proteases in the biological fluid from degrading the analyte.

The pH of the incubation buffer is chosen to maintain a significant level of specific binding of the capture reagent to the analyte being captured. The pH of the incubation buffer is preferably about 6-9.5, more preferably about 6-7. Various buffers can be employed to achieve and maintain the desired pH during this step, including borate, phosphate, carbonate, Tris-HCl or Tris-phosphate, acetate, barbital, and the like. The particular buffer employed is usually not critical, however, and in individual assays one buffer may be preferred over another.

The sample is separated from the immobilized capture reagent with a wash solution to remove uncaptured analyte from the system. The wash solution is generally a buffer. The incubation buffers described above are suitable wash solutions. The pH of the wash solution is determined as described above for the incubation buffer. In an embodiment, the pH of the wash solution is about 6-9, more preferably about 6-7. Washes can be done one or more times. Minimizing the number of washes, however, to retain molecules that bind the target molecule with low affinity increases the background noise of the assay. Preferably, the system is washed three times. The temperature of the wash solution is typically from about 0-40° C., more preferably about 4-30° C. An automated plate washer can be utilized. A cross-linking agent or other suitable agent can be added to the wash solution to covalently attach the captured analyte to the capture reagent.

Following removal of uncaptured analyte molecules from the system, the captured analyte molecules are contacted with a detecting agent, such as an antibody, preferably at a temperature of about 20-40° C., more preferably about 36-38° C. When the analyte is humanized anti-therapeutic antibody, the detecting agent is an anti-isotype antibody from a different species. If the anti-therapeutic antibodies are human IgG, for example, the detecting agent can be a murine anti-human IgG antibody. In an embodiment, the analyte is murine monoclonal antibody and the detecting agent is sheep anti-mouse IgG.

The temperature and time for contacting the analyte molecule with the detecting agent is dependent primarily on the detection means employed. For example, when horseradish peroxidase (HRP) conjugated to sheep anti-mouse IgG is used as the means for detection, the detecting agent is preferably incubated with the captured analyte for about 0.5-2 hours, more preferably about 1 hour. The system is washed as described above to remove unbound detecting agent from the system and developed by adding peroxidase substrate and incubating the plate for about 5 minutes at room temperature or until good color is visible.

In an embodiment, a molar excess of the detecting agent is added to the system after the unbound analyte has been washed from the system. The detecting agent can be a polyclonal or monoclonal antibody. In an embodiment, the antibody is a monoclonal antibody. In an embodiment, the monoclonal antibody is murine. The detecting agent can be directly or indirectly detectable. If the detecting agent is an antibody that is not directly detectable, the detecting antibody is detected by addition of a molar excess of a second, labeled antibody directed against the isotype and animal species of the detecting antibody.

The affinity of the detecting agent must be sufficiently high such that small amounts of analyte can be detected. A fluorimetric or chemiliminescent label moiety has greater sensitivity in immunoassays compared to a conventional colorimetric label. The binding affinity of the selected detecting agent must be considered in view of the binding affinity of the capture agent, such that the detecting agent does not strip the analyte from the capture reagent.

The label moiety is any detectable functionality that does not interfere with the binding of the captured analyte to the detecting agent. Examples of suitable label moieties include moieties that can be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodainine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphiatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-β-galactosidase with MUG, spin labels, bacteriophage labels, stable free radicals, and the like.

Conjugation of the label moiety to the detecting agent, such as for example an antibody, is a standard manipulative procedure in immunoassay techniques. See, for example, O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166. Conventional methods are available to bind the label moiety covalently to proteins or polypeptides. For example, coupling agents such as dialdehydes, carbodiimides, dimaleimides, bis-imidates, bis-diazotized benzidine, and the like can be used to label antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., 1962, *Nature*, 144:945; David et al., 1974, *Biochemistry*, 13:1014-1021; Pain et al., 1981, *J. Immunol Methods*, 40:219-230; and Nygren J., 1982, *Histochem. and Cytochem.*, 30:407-412. Preferred labels herein are fluorescent or chemiluminescent to increase amplification and sensitivity to about 5-10 pg/ml. In an embodiment, the label moiety is HRP.

The amount of analyte bound to the capture reagent is determined by washing away unbound detecting agent from the immobilized phase and measuring the amount of detecting agent bound to the analyte using a detection method appropriate to the label. In an embodiment, the label moiety is an enzyme. In the case of enzyme moieties, the amount of developed color is a direct measurement of the amount of captured analyte. For example, when HRP is the label moiety, color is detected by quantifying the optical density (O.D.) at 650 nm absorbance. In another embodiment, the quantity of analyte bound to the capture reagent is determined in-directly. The signal of an unlabeled detecting agent can be amplified for detection with an anti-detecting agent antibody conjugated to a label moiety. For example, the signal of an unlabeled mouse antibody that binds the target molecule can be amplified with a sheep anti-mouse IgG antibody labeled with HRP. The label moiety is detected using a detection method appropriate to the label. For example, HRP can be detected by reacting HRP with a calorimetric substrate and measuring the optical density of the reacted substrate at 650 nm absorbance.

The pH and/or temperature of the system can be varied to identify molecules that bind the target molecule.

B. ECLA

Conventional methods for ECLA can be used in the cross-screening system and methods of the invention. See, for example, U.S. Pat. Nos. 5,543,112; 5,935,779; 6,316,607, and the patents referenced therein. In an embodiment, the capture reagent and detecting reagent are mixed with the analyte molecule and incubated at room temperature. In an embodiment, the capture reagent and detecting reagent are in molar excess of the maximum molar concentration of the analyte molecule anticipated in the sample. Depending on the analyte molecule, the capture reagent may compete for binding sites with the detecting reagent yielding inaccurate results. Therefore, the final concentration of the capture reagent will normally be determined empirically to maximize the sensitivity of the assay over the range of interest. In an embodiment, the capture reagent and detecting reagent are added to the sample in about a 1:1 ratio.

The capture reagent can be an antigen, receptor, antibody, or fragment thereof. Preferably the antibody is monoclonal. In an embodiment, the capture reagent is an antibody or a mixture of different antibodies against a target antigen. In another embodiment, the capture reagent is a goat anti-human IgG antibody. The detecting agent can be a receptor, antibody, or fragment thereof. In an embodiment, the antibody is monoclonal. The monoclonal antibody can be a murine monoclonal antibody. In an embodiment, the detecting reagent is an antibody or a mixture of different antibodies against a target antigen. In another embodiment, the detecting agent is murine anti-human IgG antibody.

The incubation time can be from about 0.5 to 3 hours, more preferably 1.5-3 hours at 36-38° C. The pH of the incubation buffer is chosen to maintain a significant level of specific binding of the capture reagent and detecting agent to the analyte. In an embodiment, the pH of the incubation buffer is about 6-9.5, more preferably about 6-7. Various buffers can be employed to achieve and maintain the desired pH during this step, including borate, phosphate, carbonate, Tris-HCl or Tns-phosphate, acetate, barbital, and the like. The particular buffer employed is usually not critical, however, in individual assays one buffer may be preferred over another.

In an embodiment, the ECLA method utilizes a binding phase to immobilize the analyte complex, such as beads or microparticles. The beads or microparticles can have a diameter of 0.05 um to 200 um, more preferably 0.1 um to 100 um, more preferably 0.5 um to 10 um, and a surface component capable of binding the capture reagent. In an embodiment, the binding surface of the beads or microparticles is coated with streptavidin and the capture reagent is labeled with biotin. The microparticles can also be coated, for example, with glutathione, anti-IgG antibody, or agglutinin. The capture reagent can be biotinylated with biotinylamidocaproic acid-N-Hydroxy-succinimide ester using standard amine chemistry at a ratio from about 1:1 to about 10:1 biotin to capture reagent, more preferably from about 2:1 to about 4:1 biotin to capture reagent, more preferably about 2.5:1 biotin to capture reagent.

If the analyte is an anti-therapeutic antibody, the analyte, the capture reagent, and detecting reagent can be antibodies from the same species. In such instances, the same type of antibody can be separately utilized as both a capture reagent and detecting reagent. For example, separate batches of the same antibody are labeled, one with a component capable of binding the microparticle, such as biotin when the microparticle is coated with streptavidin, or another with or a label, such as Ori-Tag®. In an embodiment, the antibody is a therapeutic monoclonal antibody including, but are not limited to, anti-VEGF antibodies such as bevacizumab and LUCENTIS™, anti-HER2 antibodies such as HERCEPTIN® and OMNITARG™, anti-CD20 antibodies such as RITUXAN® and PRO70769, anti-IgE antibodies such as XOLAIR®, and anti-CD11a antibodies such as RAPTIVA®. In an embodiment, the capture reagent and detecting reagent are added to the analyte in about a 1:1 ratio. The analyte must bind both a capture reagent and a detecting reagent to be detected by ECLA. Analytes that bind only capture reagent can bind to the microparticle but are not detectable.

After incubating the capture reagent and detecting reagent with the analyte molecule, microparticles capable of binding the capture reagent are added to the mixture and the mixture is incubated. In an embodiment, the microparticles are coated with a molecule that binds biotin, such as streptavidin. The incubation time can be from about 0.5 to 3 hours, preferably 1.5-3 hours at 36-38° C. The pH of the incubation buffer is chosen to maintain a significant level of specific binding of the capture reagent/detecting agent/analyte molecule complex to the microparticles. The pH of the incubation buffer can be about 6-9.5, more preferably about 6-7. The incubation buffer can include an electrolyte. The electrolyte can be one or more salts or other species. In an embodiment, the electrolyte is a sodium salt or potassium salt.

The microparticles are assayed with an apparatus that contains an electrode and a photodetector, such as an IGEN M384 analyzer (IGEN International Inc., Gaithersburg, Mass.). See, for example, U.S. Pat. Nos. 5,543,112 and 5,935,779 describing apparatuses for measuring electrochemiluminescence. The label conjugated to the detecting agent is induced to emit electromagnetic radiation by stimulating the label into an excited state. Detection and/or quantitation of the analyte in a sample is typically made by comparing the luminescence of a sample to the luminescence emitted by a calibration standard developed with known amounts of the analyte and detecting agent. In an embodiment, the photodetector measures the light emitted by the label and software for analyzing data collected by the photodetector is used to calculate the concentration of analyte molecular or ECLA response (in electrochemiluminescence units (ECLU)) of the analyte molecule.

In an embodiment, the label conjugated to the detecting reagent is a metal chelate that luminesces under the electrochemical conditions imposed by ECLA. The metal can be, for example, a transition metal (such as a d-block transition metal) or a rare earth metal. In an embodiment, the metal is ruthenium, osmium, rhenium, iridium, rhodium, platinum, indium, palladium, molybdenum, technetium, copper, chromium, or tungsten. In an embodiment, the metal is ruthenium or osmium.

A ligand(s) linked to the metal of the chelate is usually heterocyclic or organic in nature, and plays a role in determining whether the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. In an embodiment, the aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate can have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis[(4,4'-carbomethoxy)-2,2'-bipyridine]2-[3-(4-methyl-2,2'-bipyridine-4-yl)propyl]-1,3-dioxolane ruthenium (II); bis(2,2'-bipyridine)[4-(butan-1-al)-4'-methyl-2,2'-bipyridine]ruthenium (II); bis(2,2'-bipyridine)[4-(4'-methyl-2,2'-bipyridine-4'-yl)-butyric acid]ruthenium (II); tris(2,2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine]ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II). Additional label moieties suitable for ECLA are described in U.S. Pat. Nos. 5,591,581; 6,271,041; 6,316,607; and 6,451,225. In an embodiment, the label moiety is Ru(bpy)$_3^{2+}$ or ORI-TAG™ NHS ester (IGEN International Inc., Gaithersburg, Mass.).

The amount of label utilized is that amount which effectively results in the emission of a detectable, and if desired, quantifiable, emission of electromagnetic energy. In an embodiment, the detecting agent is conjugated with the label, using standard amine chemistry, at a ratio from about 1:1 to about 10:1 label to detecting reagent, more preferably from about 3:1 to about 7:1 label to detecting reagent, more preferably about 5:1 label to detecting reagent.

The pH and/or temperature of the system can be varied to identify molecules that bind the target molecule.

C. Detection Limit

The detection limit for the IA and ECLA is the minimum concentration of analyte that can be detected above the background level of the respective assay. The detection limit of IA and/or ECLA can be determined by conventional methods. Below this detection limit, it is difficult to differentiate specific binding of the analyte from non-specific binding of the detecting agent. Molecules that are IA$^-$/ECLA$^-$ are considered not to have specific binding affinity for the target molecule.

The detection limit can be determined by the amount of non-specific binding of the detecting agent in the system. The background level of the IA or ECLA can be determined under the conditions of the respective assay in the absence of analyte. For example, IA and ECLA can be used to detect an analyte, such as a low affinity antibody, in a homogenous mixture. The background level in the respective assay can be determined by quantifying the signal of the detecting antibody after the system has been incubated with incubation buffer containing no analyte. IA and ECLA can also be used to screen for an analyte, such as a low affinity binding antitherapeutic antibody, in a homogenous mixture, such as serum. The background level in the respective assay can be determined by quantifying the signal of the detecting agent after the system has been incubated with serum from one or more animals that were not administered the therapeutic.

The background level can also be determined using a control analyte that does not specifically bind the target molecule. In an embodiment, the detection limit is determined using a control antibody that does not specifically bind the target antigen. For example, IA and ECLA can be used to screen the supernatant of hybridoma clones for low affinity antibodies. The background level of the respective assay can be determined by quantifying the signal of the detecting antibody after the system is incubated with a supernatant sample containing control antibodies that do not specifically bind the target antigen. In an embodiment, the control antibodies are the same isotype as the antibodies being produced by the hybridoma clones of interest.

Reducing the background level of the system reduces the detection limit thereby increasing the sensitivity of the assay. There are a number of ways the background level of the IA or ECLA can be reduced including, but not limited to, increasing the length of washes, adding additional washes, selecting a different wash buffer, selecting a solid phase of a different material, selecting a different blocking buffer, selecting a different detecting agent, selecting beads or microparticles with a lower autofluorescence level, reducing incubation times, changing the pH of one or more buffers, changing incubation temperature, or any combination thereof. With respect to ECLA specifically, employing paramagnetic beads in association with a magnetic electrode can reduce the background.

The detection limit for IA and/or ECLA may require optimization to ensure the detection limit is not excluding analyte molecules with a desired characteristic, or to ensure that undesired molecules are excluded. For example, the binding affinities of randomly selected IA$^-$/ECLA$^-$ analyte molecules can be determined. Randomly selected IA$^-$/ECLA$^-$ analyte molecules found to have a binding affinity for the target molecule of about $10^{-2}$ may indicate the detection limit is set too high and that lowering the IA and/or ELISA detection limit may identify additional analyte molecules with the desired low binding affinity for the target molecule.

D. Determination of Binding Affinity

Candidate low or high affinity analyte molecules are confirmed as low or high affinity analyte molecules based on their dissociation rate constant ($K_{dissoc}$) for the target molecule or equilibrium dissociation constant ($K_D$). Binding affinities of candidate molecules selected from the enriched pool of candidate molecules generated by the cross-screening system and methods of the invention can be confirmed by conventional equilibrium or kinetic methods. Examples include, but are not limited to, competitive ELISA, equilibrium dialysis, RIA, surface plasmon resonance such as BIACORE® (Biacore Inc., Piscataway, N.J.), affinity chromatography, and ECLA. See, for example, *Current Protocols in Molecular Biology*, Ausbul et al. eds., Wiley & Sons, 2003; *Current Protocols in Immunology*, Bierer et al. eds, Wiley & Sons, 2003; and U.S. Pat. Nos. 5,543,112; 5,935,779; and 6,143,574. In an embodiment, the binding affinity is determined by BIACORE® analysis (see Example 3 below).

A high $K_{dissoc}$ is indicative of low binding affinity. An analyte molecule with a $K_{dissoc}$ greater then $10^{-6}$ for the target molecule or $K_D$ equal to or greater than $10^{-8}$ M, is identified as a molecule having low binding affinity for the target molecule. In an embodiment, the $K_{dissoc}$ of the candidate low affinity analyte molecule for the target molecule is $10^{-5}$ or greater, more preferably $10^{-4}$ or greater, more preferably $10^{-3}$ or greater, and more preferably $10^{-2}$ or greater. In an embodiment, the $K_D$ of the candidate low affinity analyte molecule for the target molecule is about $10^{-6}$ M, about $10^{-7}$ M, or about $10^{-8}$ M.

E. Isotyping

The isotypes of the heavy and light chains of low affinity binding antibodies (analyte molecules) identified by the cross-screening system and methods of the invention can be determined by conventional methods, such as ELISA utilizing anti-isotype specific antibodies. See, for example, *Current Protocols in Immunology*, Bierer et al. eds, Wiley & Sons, 2003. In an embodiment, the antibodies are alkaline phosphatase or HRP-conjugated anti-mouse or anti-human antibodies. In an embodiment, a panel of anti-heavy chain isotype specific antibodies anti-isotype specific antibodies is employed. The panel of antibodies can include anti-heavy chain anti-isotype specific IgG, IgE, IgA, and IgM antibodies. In an embodiment, the panel of antibodies includes at least anti-IgG1, IgG2a, IgG2b, or IgG3 isotype specific antibodies.

F. Uses

The cross-screening system and methods of the invention have many applications. The methods of the invention are particularly useful for identifying analyte molecules that bind a target molecule. For example, the methods are useful for identifying polypeptides or small molecules that bind a specific receptor, or antibodies that bind a specific antigen. In an embodiment, a receptor, antibody, or fragment thereof is expressed on a phage. In another embodiment, the antigen is a polypeptide or monoclonal antibody having therapeutic activity. For example, the monoclonal antibody can be anti-VEGF antibody such as bevacizumab and LUCENTIS™, anti-HER2 antibody such as HERCEPTIN® and OMNI-TARG™, anti-CD20 antibody such as RITUXAN® and PRO70769, anti-IgE antibody such as XOLAIR®, and anti-CD11a antibody such as RAPTIVA®. In an embodiment, the target antigen is monoclonal antibody 2H7. In another embodiment, the target antigen is monoclonal antibody bevacizumab. The pH and/or temperature of the system can be varied to identify molecules that bind the target molecule.

The cross-screening system and methods of the invention are particularly useful to detect small amounts of analyte molecule in a sample. Preferably the analyte molecule is an antibody. For example, the cross-screening system and methods of the invention can be used to identify a hybridoma producing antibodies that have high affinity for the target molecule but the concentration of antibodies in the supernatant is low. The concentration of antibodies in the supernatant can be below the detection limit of the individual IA or ECLA assay, but not the detection limit of the cross-screening system and methods of the invention.

The methods of the invention can be used to enrich a pool of analyte molecules for a desired characteristic. In an embodiment, the analyte molecules are antibodies. In an embodiment, the desired characteristic is binding affinity ($IA^-/ECLA^+$, $IA_+/ECLA^+$, and $IA^+/ECLA^+$) for the target molecule. In another embodiment, the desired characteristic is high binding affinity for a target molecule ($IA^+/ECLA^+$ or $IA^+/ECLA^-$). For example, a small molecule library can be screened for candidate library members that bind a target receptor with high affinity. Similarly, a library of receptors, antibodies, or fragments thereof can be screened for candidate library members that bind a target polypeptide with high affinity. In another embodiment, the desired characteristic is low binding affinity for a target molecule ($IA^-/ECLA^+$), such as for example, an antigen. The candidate molecules can be confirmed as high affinity or low affinity analyte molecules respectively, by determining a specific binding affinity of the analyte molecules for the target antigen.

Low affinity antibodies are needed, for example, in antitherapeutic antibody assays required for regulatory approval of biological therapeutics. Immune responses are polyclonal; therefore, anti-therapeutic antibodies generated against a biological therapeutic can target different regions of the therapeutic or demonstrate different binding affinities and isotypes. In clinical trials, for example, a panel of anti-therapeutic antibodies that mimics the polyclonal nature of an immune response to the biological therapeutic undergoing clinical testing can be used to assess performance of an anti-therapeutic antibody assay. Low affinity antibodies identified by the cross-screening system and methods of the invention can be used to construct such a panel of antibodies. In an embodiment, the cross-screening system and methods of the invention are used to screen hybridoma clones for antibodies that bind a target antigen with low affinity. In an embodiment, the target antigen is a therapeutic monoclonal antibody.

In clinical trials for example, detection of antibodies to a biological therapeutic at an early stage in the trial is important for assessing the safety and efficacy of the therapeutic. In an embodiment, the methods of the invention are used to screen serum from a patient about to receive or who is receiving a biological therapeutic, such as a polypeptide or monoclonal antibody, for anti-therapeutic antibodies.

Low affinity antibodies are also useful in drug discovery methods. For example, it can be difficult to generate antibodies with high binding affinity for a therapeutic target. Low affinity antibodies can serve as a starting point for developing affinity matured antibodies. In an embodiment, antibodies are cross-screened utilizing the methods of the invention for analyte molecules exhibiting low binding affinity for the therapeutic target. Selected low affinity antibodies are affinity matured to produce therapeutic antibodies. In an embodiment, the antibodies are expressed on phage. In another embodiment, the antibodies are members of a phage library.

Having generally described the invention, the same will be more readily understood by reference to the following examples, which are provided by way of illustration and are not intended as limiting.

All publications (including patents and patent applications) cited herein are hereby incorporated in their entirety by reference.

EXAMPLE 1

Screening Hybridomas for Low Affinity Anti-2H7 Antibodies

Hybridoma supernatants were screened for production of low affinity anti-2H7 antibodies using cross-screening methods employing ELISA and ECLA. A workflow diagram of an embodiment of a hybridoma screening strategy is shown in FIG. 1.

Hybridoma Production

BALB/c mice were immunized and boosted 10 times with 0.5 μg 2H7 resuspended in monophosphoryl lipid A/trehalose dicorynomycolate adjuvant (Corixa). The suspension was injected in each hind footpad at 3 to 4 days intervals. Three days after final boost, poptileal lymph nodes were fused with cells of the myeloma cell line, P3X63Ag.U.1 (ATCC, Manassas, Va.). Fused cells were selected by hypoxanthin-aminopterin-thymidine (HAT) medium selection.

ECLA Screening

Supernatants from hybridoma cultures were screened for low affinity anti-2H7 antibodies by plotting ECLA responses versus ELISA responses. ECLA was performed as described in Baker et al., 2002, *Trends in Biotechnol.*, 20:149-156.

Briefly, separate batches of 2H7 antibodies were labeled with biotin or Ori-tag (Igen International Inc, Gaithersburg, Md.). 2H7 was biotinlylated with biotinylamiocaproic acid-N-hydroxy-succinimid ester (Organics Inc.) using standard amine based chemistry at target ratio of 2.5:1 biotin to 2H7. 2H7 was labeled with ORI-TAG NHS ester according to the manufacturer's instructions at a targeted ratio of 5:1 ORI-TAG to 2H7. A master working solution was prepared by mixing biotinylated 2H7 and Ori-tag labeled 2H7 in a 1:1 ratio. The final concentration of each labeled antigen in the master working solution was 1 μg/ml.

A panel of monoclonal antibodies was created by adding 50 μl of master working solution and 50 μl of supernatant from individual hybridoma clones to a 96-well round-bottom polypropylene plate. Each well in the plate contained supernatant from a single hybridoma clone. The plate was incubated at room temperature in the dark for two hours with a gentle agitation 10 μg of streptavidin coated magnetic beads in a volume of 100 μl was added to each well. The plate was incubated for another one hour at room temperature in the dark with a gentle agitation. Post-incubation, the plates were read on an IGEN M384 analyzer using the following protocol parameters: bead type is set at 2.80 microns, aspiration volume of 200 μl, POP of 0 mv, gain of 1, wash volume of 700 μl, clean cycle of 2, wash speed of 200 ml/sec. Data was collected and reported in electrochemiluminescence units (ECLU).

HAT medium was used a control. To be detected by ECLA, the analyte molecule must bind both a capture reagent and a detecting agent. Anti-2H7 antibodies (analyte molecules) from supernatant culture that formed a complex with both capture reagent and detecting agent were detected in the assay, (ECLA$^+$). Anti-2H7 antibodies from the supernatant culture that bound only capture reagent or only detecting reagent were not detected.

ELISA Screening

ELISA was performed generally as described in Baker et al., 2002, *Trends in Biotechnol.*, 20:149-156. Briefly, a 384-well Greiner flat bottom plate was coated with 50 μl of goat anti-human IgG Fc specific (Cappel #55071) at a concentration of 2 μg/ml in coating buffer (50 μM carbonate buffer, pH 9.6). The plate was sealed and stored at 4° C. overnight. After removing the coating solution, 100 μl of blocking solution containing 2% of bovine serum albumin in PBS was added to each well. The plate was incubated at room temperature for one hour with agitation and then washed three times with PBS/0.05% Tween-20.

After the washing step, 50 μl of antigen solution (0.4 μg/ml 2H7 in PBS containing 0.5% bovine serum albumin) was added to each well and the plate was incubated at room temperature for one hour with agitation. The plated was washed three times with PBS/0.05% Tween-20. 35 μl of supernatant from individual hybridoma clones was added such that each well in the plate contained supernatant from a single hybridoma clone. The plate was incubated for one hour at room temperature and washed three times with PBS/0.05% Tween-20.

After the washing step, 50 μl of a 1:1000 dilution of sheep anti-mouse IgG HRP (no cross reactivity to human IgG, Cappel #55569) in PBS containing 0.5% bovine serum albumin and 0.1% Tween-20 was added to each well. The plate was incubated at room temperature for one hour with agitation, washed three times with PBS/0.05% Tween-20, rinsed with water, and shaken dry. The plate was developed by adding 40 μl of TMB Microwell Peroxidase (tetramethylbenzidine) substrate (BioFX #TMBT-0100-01) to each well in the plate and incubating the plate for 5 minutes at room temperature or until a good color was visible. Development was stopped by adding 40 μl of the Stop solution (BioFX #BSTP-0100-01) to each well, plates were read on a Sunrise plate reader (Tecan US, Research Triangle Park, N.C.) at 650 nm.

Identification of Low Affinity Antibodies

Figure 2:
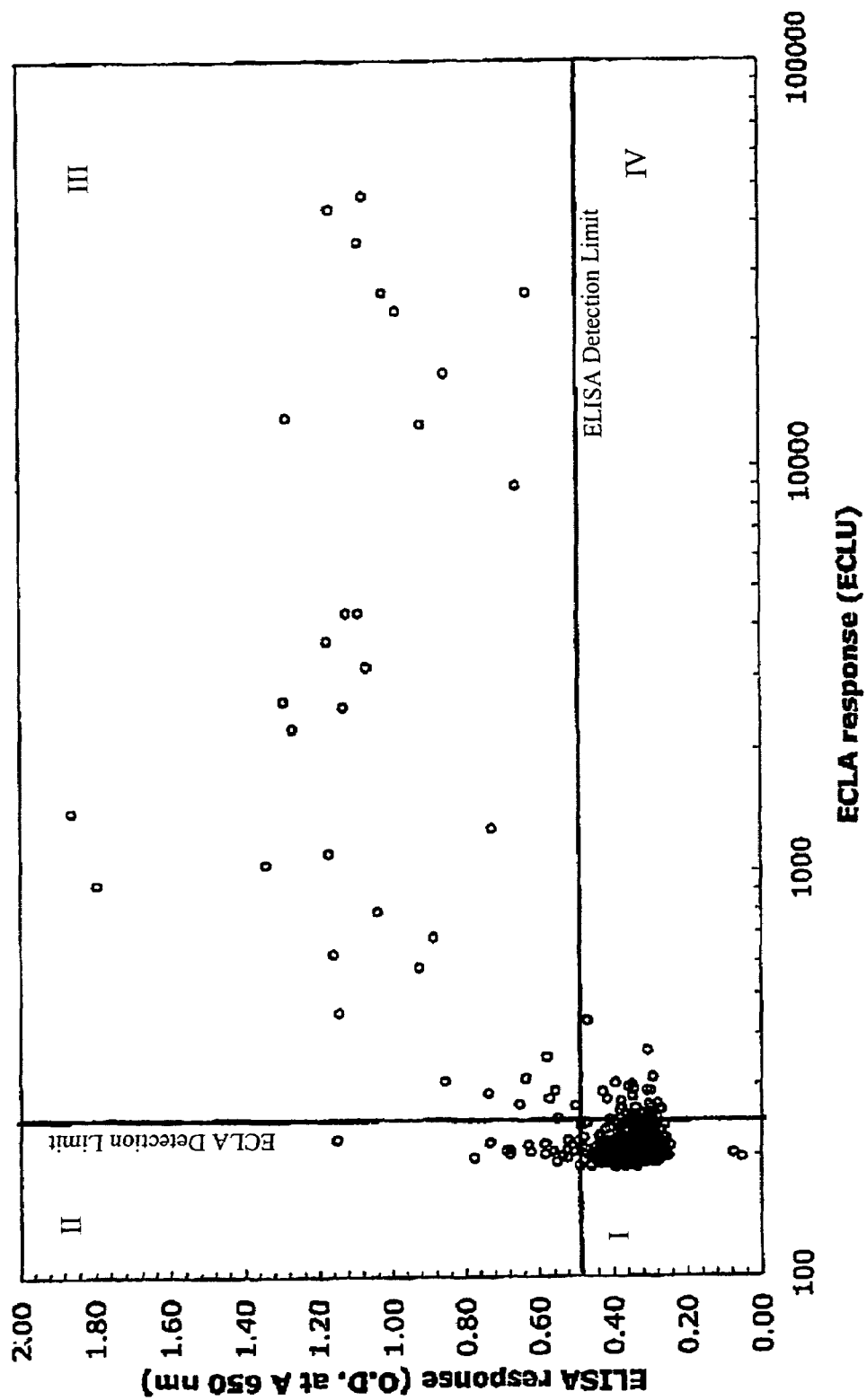
FIG. 2 is a plot showing results of cross-screening a pool of anti-2H7 antibodies produced from hybridomas. The ECLA response (ECLU) is plotted against the ELISA response (O.D. at 650 nm). Antibodies in area I (ECLA$^-$/ELISA$^-$) represent antibodies that either do not specifically bind 2H7, or where binding was not detected by either assay. Antibodies in area II (ELISA$^+$/ECLA$^-$) and III (ECLA$^+$/ELISA$^+$) represent candidate high binding affinity anti-2H7 antibodies. Antibodies in area IV (ECLA$^+$/ELISA$^-$) represent candidate low affinity anti-2H7 antibodies. Antibodies in area IV represent a population of anti-2H7 antibodies not detected by ELISA. Antibodies that are ECLA$^-$/ELISA$^+$ include candidate antibodies that bind the target anti-2H7 at a binding site that is masked or altered in the ECLA assay, for example, by biotin or a chemical label employed in ECLA.

Low affinity anti-2H7 antibodies were identified by plotting ECLA responses (ECLU) against ELISA responses (O.D. at 650 nm) for each respective hybridoma supernatant (FIG. 2). The detection limit for ELISA was set at O.D. 0.5. HAT medium was used as a control in ECLA to establish a detection limit of 250 ECLU.

Detection limits for ECLA and ELISA were used to establish a four quadrant grid on the ECLA:ELISA plot (FIG. 2). Lines depicting detection limits form the boundaries of four quadrants. Antibodies in area I (ECLA$^-$/ELISA$^-$) represent antibodies that did not bind 2H7 or had binding that was not detected by either ELISA or ECLA. Antibodies in area III (ECLA$^+$/ELISA$^+$) represent candidate high affinity anti-2H7 antibodies. Antibodies in area II (ECLA$^-$/ELISA$^+$) represent candidate high affinity anti-2H7 antibodies that are believed to bind epitopes masked or altered by biotinlyation of 2H7 and/or labeling of 2H7 with Ori-Tag. Antibodies in area III (ECLA$^+$/ELISA$^+$) represent candidate low affinity anti-2H7 antibodies. Antibodies in area IV represent a population of anti-2H7 antibodies not detected by ELISA. These antibodies may have been washed off the plate during the multiple wash steps in ELISA or had an ELISA response less than 0.5. Antibodies in area IV presumptively produced low affinity antibodies. While Area IV is enriched in low affinity antibodies, it may also contain high affinity antibodies present in low concentration in the supernatant.

EXAMPLE 2

Biacore Analysis of Low Affinity Anti-2H7 Antibodies

A number of hybridoma clones producing antibodies in quadrants I, II, III, or IV in Example 1 were selected for further characterization and confirmation of specific binding affinity. Dissociation rate constants ($K_{dissoc}$) for antibodies produced by the selected hybridoma clones were determined by Biacore analysis.

The analysis was performed on a Biacore 3000 (USA Biacore, Inc., Piscataway, N.J.). The monoclonal antibody 2H7 was immobilized on a CM5 sensor chip in a flow cell. In brief, the flow cell was activated by injecting 35 μl of a solution containing equal volumes of 11.5 mg/ml of N-hydroxysuccinimide (NHS) and 7.5 mg/ml of 1-ethyl-3-(3-dimethylaminopropyl)carbodiimide hydrochloride (EDC). Following activation of the flow cell, 2H7 in sodium acetate (pH 5.0) was injected manually to reach a response of approximately 500 RU on the chip. Thirty-five μl of 1 M ethanolamine hydrocholoride-NaOH (pH 8.0) was injected at a flow rate of 5 μl/minute to block any un-reacted activated sites on the flow cell. The final concentration of immobilized 2H7 after ethanolamine blocking was 556 RU. A different flow cell was used as an in-line reference cell. The reference flow cell was activated as described above and immediately blocked with a 3511 injection of 1 M ethanolamine hydrocholoride-NaOH (pH 8.0) at a flow rate of 5 μl/minute.

After the sensor chip was prepared, 120 μl of supernatant from each hybridoma clone was injected over the flow cells at a flow rate of 30 μl/minute. Dissociation was allowed for 6 minutes. The chip was then regenerated with a consecutive injection of 50 μl each of 10 mM glycine, pH 2.0 and 10 mM glycine, pH 2.5.

Dissociation rate constants were obtained using a separate $k_{assoc}/k_{dissoc}$ fitting model with BIAevaluation 3.2 software provided by the manufacturer. The fitting model assumed 1:1 binding.

Figure 3:
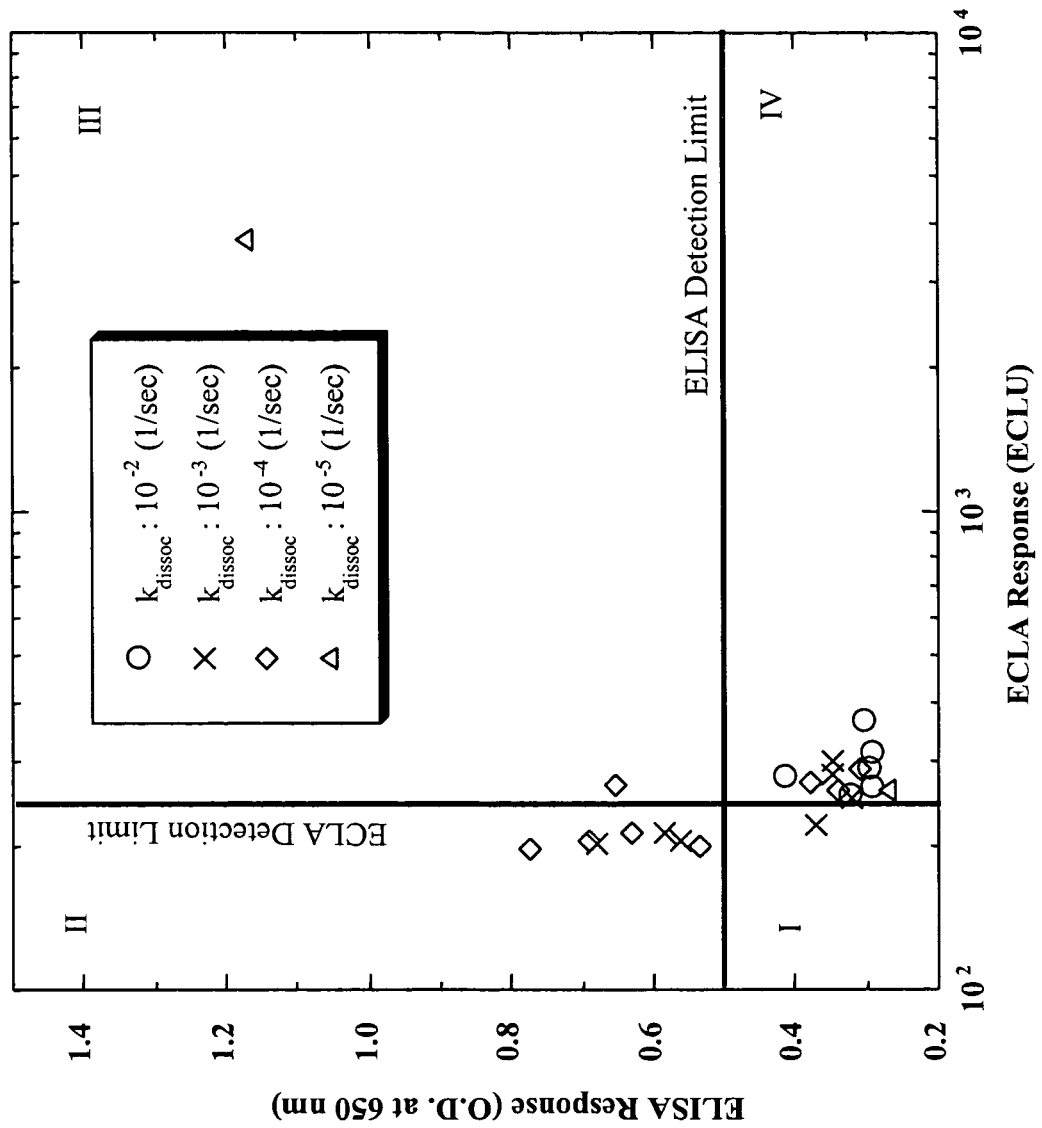
FIG. 3 shows equilibrium dissociation constants ($K_{dissoc}$) of select antibodies plotted according to ECLA response and ELISA response. Dissociation rate constants of antibodies in area II (ECLA$^-$/ELISA$^+$) were in the range of about $10^{-3}$ to $10^{-5}$ 1/sec; those of antibodies in area III (ECLA$^+$/ELISA$^+$) were about $10^{-4}$ 1/sec or less (Table 1 and FIG. 3); those of antibodies in area IV (ECLA$^+$/ELISA$^-$) were in the range of about $10^{-2}$ to $10^{-4}$ 1/sec (Table 1 and FIG. 3). Antibodies with a $K_{dissoc}$ of about $10^{-2}$ 1/sec were found only in area IV. The $K_{dissoc}$ of one area IV antibody was $10^{-5}$ 1/sec.

$K_{dissoc}$ calculated for each of the selected antibodies was plotted according to ECLA responses and ELISA responses described in Example 1 (FIG. 2). Antibodies in area II (ECLA$^-$/ELISA$^+$) were found to have a $K_{dissoc}$ in the range of $10^{-3}$-$10^{-5}$ 1/sec (Table 1 and FIG. 3). Antibodies in area III (ECLA$^+$/ELISA$^+$) were found to have a $K_{dissoc}$ of $10^{-4}$ or less (Table 1 and FIG. 3). Antibodies in area IV (ECLA$^+$/ELISA$^-$) were found to have a $K_{dissoc}$ in the range of $10^{-2}$-$10_{-5}$ (Table 1 and FIG. 3). Antibodies with a $K_{dissoc}$ of $10^{-2}$ were only found in area IV. The antibodies in area I (ECLA$^-$/ELISA$^-$) presumably did not specifically bind 2H7.

TABLE 1

| Sample Number | ECLA response (ECLU) | ELISA response (O.D. at 650 nm) | Positive in | $k_{dissoc}$ (1/s)$^a$ | Heavy Chain Isotype | Light Chain |
|---|---|---|---|---|---|---|
| 1 | 269 | 0.653 | Both | 8.46E−04 | IgG1/IgG2b** | kappa |
| 2 | 277 | 0.572 | Both | * | IgG1 | kappa |
| 34 | 220 | 0.373 | None | 6.64E−03 | * | * |
| 93 | 252 | 0.354 | ECLA | * | * | * |
| 114 | 3695 | 1.175 | Both | 3.39E−05 | IgG1 | kappa |
| 141 | 293 | 0.346 | ECLA | * | IgG1 | kappa |
| 205 | 197 | 0.776 | ELISA | 2.31E−04 | IgG1 | kappa |
| 389 | 288 | 0.430 | ECLA | * | IgG1 | kappa |
| 421 | 201 | 0.582 | ELISA | * | * | * |
| 425 | 199 | 0.534 | ELISA | 4.54E−04 | IgG1 | kappa |
| 429 | 263 | 0.296 | ECLA | 0.030 | * | * |
| 452 | 262 | 0.340 | ECLA | 2.19E−04 | * | * |
| 471 | 213 | 0.629 | ELISA | 8.99E−04 | IgG1 | lambda |
| 492 | 214 | 0.584 | ELISA | 2.46E−03 | IgG2b | kappa |
| 517 | 432 | 0.469 | ECLA | * | * | * |
| 567 | 269 | 0.281 | ECLA | * | * | * |
| 574 | 299 | 0.350 | ECLA | 1.37E−03 | * | * |
| 634 | 296 | 0.359 | ECLA | * | * | * |
| 664 | 205 | 0.561 | ELISA | 1.74E−03 | * | * |
| 705 | 260 | 0.384 | ECLA | * | * | * |
| 729 | 206 | 0.689 | ELISA | 9.84E−04 | IgG1 | lambda |
| 731 | 202 | 0.679 | ELISA | 5.11E−03 | * | * |
| 740 | 261 | 0.273 | ECLA | 4.20E−05 | IgG1 | kappa |
| 750 | 252 | 0.322 | ECLA | 1.37E−03 | * | * |
| 765 | 263 | 0.377 | ECLA | * | IgG3 | kappa |
| 770 | 253 | 0.344 | ECLA | * | IgG2a | kappa |
| 786 | 302 | 0.394 | ECLA | * | * | * |
| 807 | 364 | 0.308 | ECLA | 1.01E−02 | * | * |
| 824 | 281 | 0.348 | ECLA | 1.93E−03 | * | * |
| 876 | 290 | 0.300 | ECLA | 1.52E−02 | IgG3 | kappa |
| 886 | 313 | 0.294 | ECLA | 1.33E−02 | * | * |
| 888 | 277 | 0.417 | ECLA | 1.64E−02 | * | * |
| 902 | 256 | 0.299 | ECLA | * | * | * |
| 911 | 267 | 0.304 | ECLA | * | IgG2b | kappa |
| 919 | 255 | 0.324 | ECLA | 0.017 | * | * |
| 939 | 290 | 0.310 | ECLA | 7.91E−04 | IgG1 | * |

$^a$measured by Biacore analysis
*not measurable due to a low concentration and/or exceeding assay limitation
**sample contained two different heavy chain isotypes, IgG1 and IgG2b.

Antibodies that demonstrated a $K_{dissoc}$ greater than about $10^{-5}$ were identified as low affinity antibodies. As shown in Table 1 and FIG. 3, all but one of the identified low affinity antibodies were ECLA+/ELISA− or ECLA−/ELISA+. One antibody in area I (ECLA−/ELISA−) was found to have a $K_{dissoc}$ of $10^{-3}$, suggesting the detection limit for ECLA may have been set too high. Lowering the ECLA detection limit may have identified additional low affinity anti-2H7 antibodies. One antibody in area IV was found to have a $K_{dissoc}$ of $10^{-5}$, suggesting the concentration of anti-2H7 antibody in the hybridoma supernatant producing this antibody was low.

EXAMPLE 3

Isotyping of Low Affinity Anti-2H7 Antibodies

Isotypes were determined for antibodies produced by the hybridoma clones selected for further characterization in Example 2. An ELISA based antibody isotyping assay was performed Briefly, a polypropylene 96-well microtiter plate was coated with 50 µl of isotype specific goat anti-mouse Ig (Southern Biotech, Pittsburgh, Pa.) and incubated overnight at 4° C.

The plate was washed with wash buffer (PBS with 0.05% Tween-20) and blocked with 200 µl of 2% BSA in PBS for one hour at room temperature. The plates were washed with wash buffer three times and 100 µl of hybridoma culture supernatant was added to the wells. The plate was incubated for 30 minutes at room temperature and washed three times. Fifty µl of HRP goat anti-mouse IgG Fc specific (ICN) was added to each well and the plate was incubated for 30 minutes at room temperature. The plate was developed with HRP substrate as described for Example 1. Absorbance was measured as described for Example 1.

Figure 4:
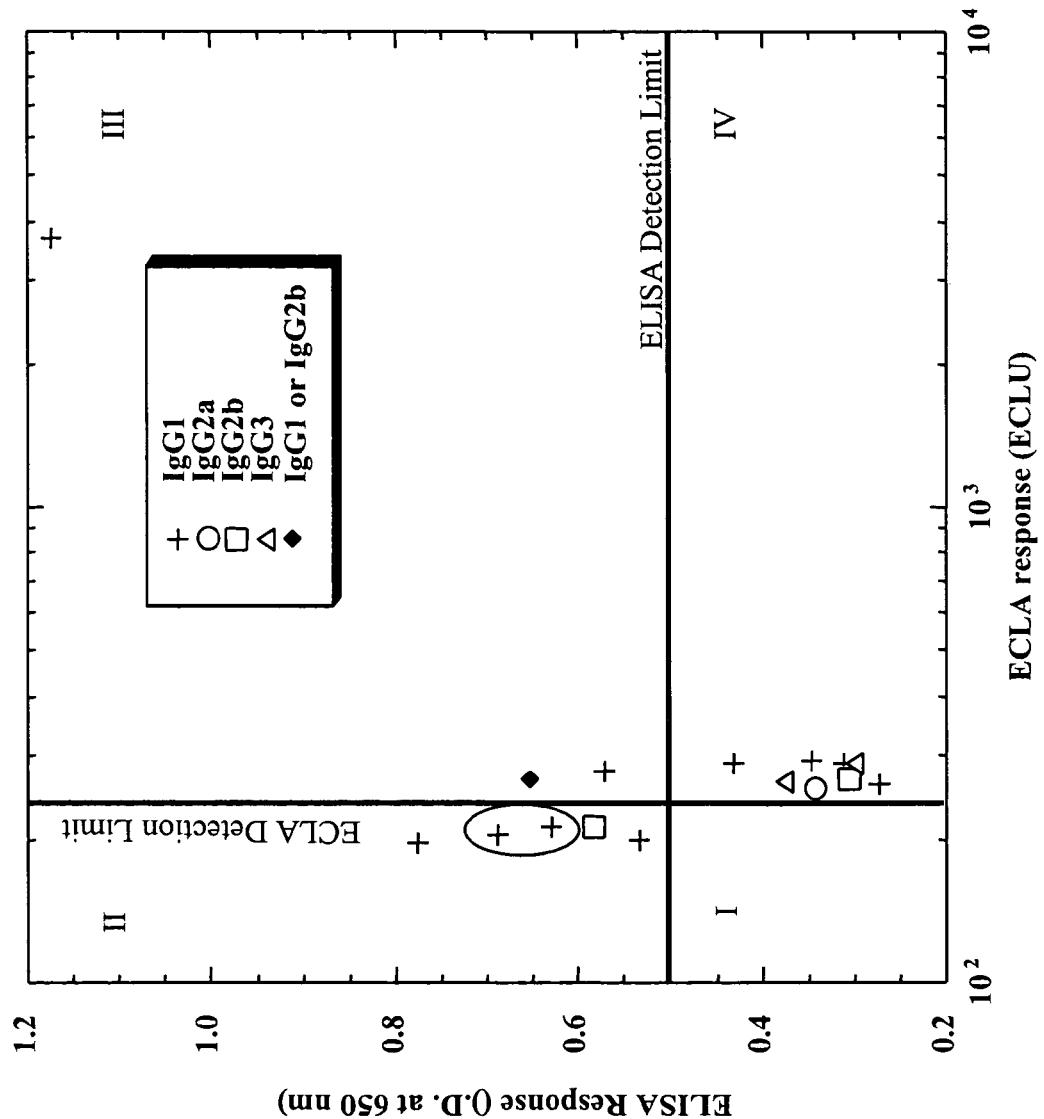
FIG. 4 shows heavy chain isotypes of selected antibodies plotted according to ECLA response and ELISA response. All the tested antibodies contained a kappa light chain, except for two antibodies in area II. These two antibodies contained a lambda light chain and are circled in FIG. 4. Antibodies in area II (ECLA$^-$/ELISA$^+$) contained heavy chain isotypes of IgG1 or IgG2b. Antibodies in area III (ECLA$^+$/ELISA$^+$) contained heavy chain isotypes of IgG1 or IgG2b. Antibodies in area IV (ECLA$^+$/ELISA$^-$) contained heavy chain isotypes of IgG, IgG2a, IgG2b, or IgG3.

Heavy chain isotypes of antibodies produced by the selected hybridoma clones were plotted according to ECLA responses and ELISA responses as described for Example 1 (FIG. 4). All antibodies tested showed a kappa light chain, except for two antibodies in area II (Table 1). These two antibodies showed a lambda light chain and are circled in FIG. 4. Antibodies in area II (ECLA−/ELISA+) were found to have heavy chain isotypes of IgG1 or IgG2b (Table 1 and FIG. 4). Antibodies in area III (ECLA+/ELISA+) were found to have heavy chain isotypes of IgG1 or IgG2b (Table 1 and FIG. 4). Antibodies in area IV (ECLA+/ELISA−) were found to have heavy chain isotypes of IgG, IgG2a, IgG2b, or IgG3 (Table 1 and FIG. 4).

EXAMPLE 4

Screening Hybridomas for Low Affinity Anti-bevacizumab Antibodies

Hybridoma supernatants were screened for production of low affinity anti-bevacizumab antibodies (Genentech Inc., South San Francisco, Calif.) using the ELISA/ECLA cross-screening method described in Example 1.

BALB/c mice were immunized and boosted with bevacizumab as described in Example 1. Three days after final boost, poptileal lymph nodes were fused with cells of the myeloma cell line, P3X63Ag.U.1 (ATCC, Manassas, Va.). Fused cells were selected by hypoxanthin-aminopterin-thymidine (HAT) medium selection.

Supernatants from hybridoma cultures were screened for low affinity anti-bevacizumab antibodies by plotting ECLA responses versus ELISA responses. ECLA screening and ELISA screening was performed as described in Example 1.

An enriched pool of candidate low affinity anti-bevacizumab antibodies was generated by plotting ECLA responses verses ELISA responses as described in Example 1. The detection limit for ELISA was set at O.D. 0.5. The detection limit for ECLA was set at 300 ECLU. As described in Example 1, lines depicting detection limits form the boundaries of four quadrants: area I (ELISA−/ECLA−), area II (ELISA+/ECLA−), area III (ELISA+/ECLA+), and area IV (ELISA−/ECLA+). See, for example, FIG. 1. Antibodies in area IV (ELISA−/ECLA+) represent a population of candidate low affinity anti-bevacizumab monoclonal antibodies not detected by ELISA. Antibodies from two hybridoma clones (4B9 and 8F6) were identified as ELISA−/ECLA+ (Table 2). These antibodies are candidate low affinity anti-bevacizumab monoclonal antibodies.

TABLE 2

| Clone | ELISA (O.D.) |        | ECLA (ECLU) |       |
|-------|--------------|--------|-------------|-------|
| 4B9   | 0.459        | ELISA− | 14101       | ELCA+ |
| 4D7   | 0.967        | ELISA+ | 22815       | ELCA+ |
| 5E1.  | 0.987        | ELISA+ | 13334       | ELCA+ |
| 6C2   | 1.005        | ELISA+ | 25270       | ELCA+ |
| 6F11  | 0.930        | ELISA+ | 1834        | ELCA+ |
| 8F6   | 0.474        | ELISA− | 3094        | ELCA+ |

Specific binding affinities of candidate low affinity antibodies in area IV were determined. Dissociation rate constants ($K_{dissoc}$) for the antibodies were determined by Biacore analysis as described in Example 2. A fast off rate ($K_{dissoc}$) typically correlates with low binding affinity. Antibodies that demonstrated a $K_{dissoc}$ greater than about $10^{-5}$ were identified as low affinity anti-bevacizumab antibodies. Clones 4B9 and 8F6 were identified as producing low affinity anti-bevacizumab antibodies (Table 3).

Figure 5:
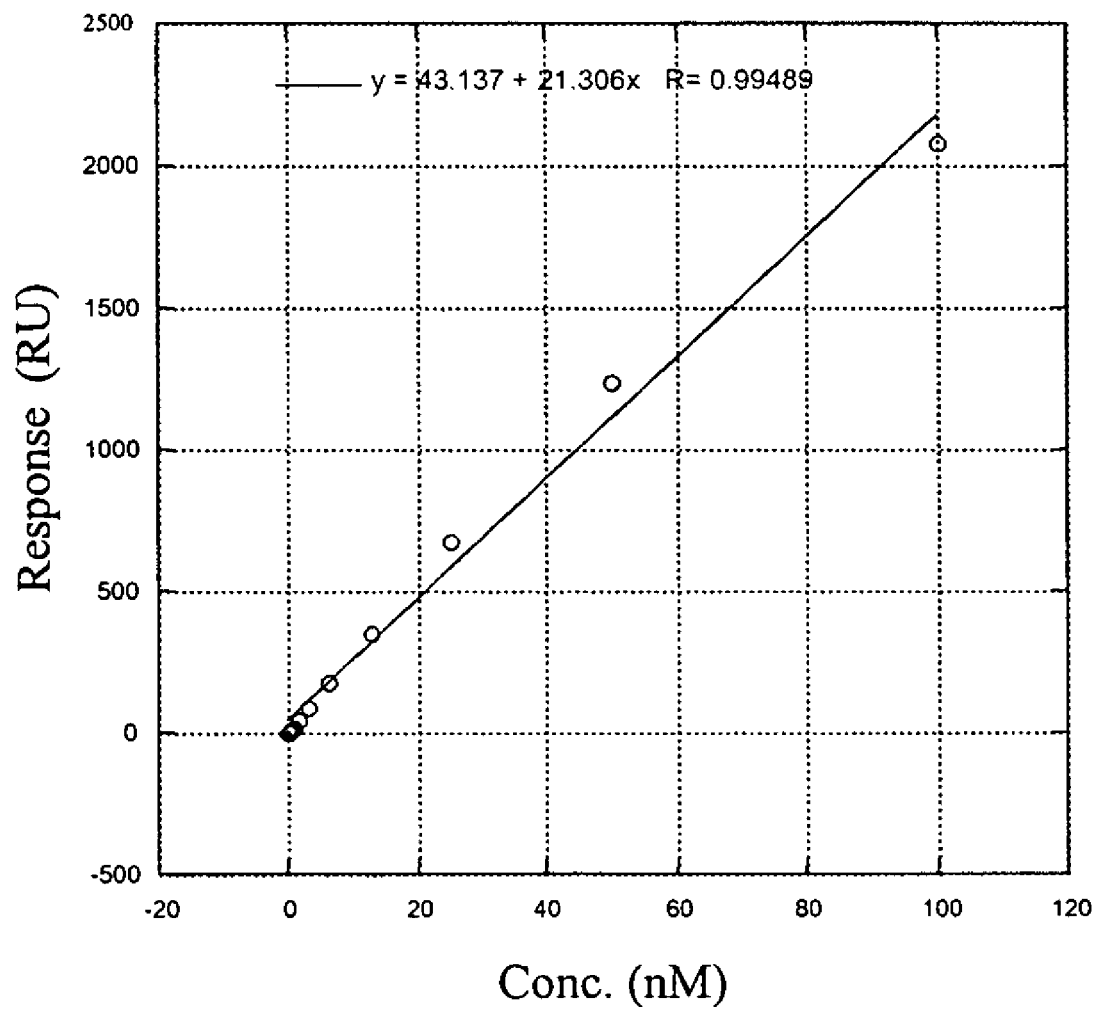
FIG. 5 shows a standard curve for anti-bevacizumab polyclonal antibody binding to bevacizumab in a Biacore assay. The concentration of antibody (nM) is plotted versus response (RU).

While area IV (ELISA−/ECLA+) is enriched in low affinity antibodies, it may also contain high affinity antibodies present in low concentration in the supernatant. To confirm identification of hybridoma clones producing low affinity antibodies, the concentration of monoclonal antibodies in the supernatant from the hybridoma clones was determined by Biacore analysis. Known concentrations of purified cynomologus monkey anti-bevacizumab polyclonal antibody were analyzed by Biacore as described in Example 2. A standard curve was generated by plotting the binding of the polyclonal antibody to bevacizumab in Biacore versus polyclonal antibody concentration and calculating the slope of the curve (FIG. 5).

The concentration of monoclonal antibodies in supernatant from the individual hybridoma clones was calculated using the standard curve and this concentration was used to calculate dissociation rates constants ($K_{dissoc}$) association rate constants ($K_{assoc}$), and equilibrium dissociation constants ($K_D$) (Table 3). The equilibrium constants and rate constants were obtained using BIAevaluation 3.2 software provided by the manufacturer. Dissociation rate constants were obtained using a $K_{assoc}/K_{dissoc}$ fitting model with the BIAevaluation 3.2 software. The fitting model assumed 1:1 binding. Antibodies that demonstrated a $K_D$ equal to or greater than about $10^{-8}$ M were confirmed as low affinity anti-bevacizumab antibodies. Clones 4B9 and 8F6 were confirmed as producing low affinity anti-bevacizumab antibodies (Table 3).

TABLE 3

| Clone | $K_{assoc}$ (1/Ms) | $K_{dissoc}$ (1/s) | $K_D$ (M) | Estimated concentration in the supernatant* (nM) |
|---|---|---|---|---|
| 4B9 | 6.40E+02 | 3.47E-05 | 5.42E-08 | 27.3 |
| 4D7 | 3.30E+05 | 8.32E-05 | 2.52E-10 | 98.1 |
| 5E1 | 2.96E+05 | 5.85E-05 | 1.98E-10 | 108.8 |
| 6C2 | 3.08E+05 | 8.88E-06 | 2.88E-11 | 59.8 |
| 6F11 | 8.04E+04 | 1.04E-04 | 1.29E-09 | 19.9 |
| 8F6 | 5.87E+03 | 3.65E-04 | 6.22E-08 | 4 |

*Concentrations were estimated using a standard curve generated with purified cynomolgus monkey anti-bevacizumab polyclonal antibodies with Biacore (see FIG. 5).

We claim:

1. A method of enriching a pool of analyte molecules with candidate analyte molecules that selectively bind a target molecule, comprising:
   (a) determining electrochemiluminescence assay (ECLA) responses for individual members of a pool of analyte molecules binding a target molecule;
   (b) applying a detection limit to the analysis of the ECLA responses, wherein an ECLA response equal to or greater than the ECLA detection limit identifies an electrochemiluminescence assay positive (ECLA+) analyte molecule and an ECLA response less than the ECLA detection limit identifies an electrochemiluminescence assay negative (ECLA−) analyte molecule;
   (c) determining immunoassay (IA) responses for individual members of the pool of analyte molecules binding the target molecule;
   (d) applying a detection limit to the analysis of the IA responses, wherein an IA response equal to or greater than the IA detection limit is immunoassay positive (IA+) and an IA response less than the IA detection limit is immunoassay negative (IA−);
   (e) generating a pool of candidate analyte molecules comprising:
      (i) immunoassay negative and electrochemiluminescence assay positive molecules (IA−/ECLA+), and enriched for low affinity analyte molecules;
      (ii) immunoassay positive and electrochemiluminescence assay positive molecules (IA+/ECLA+) or immunoassay positive and electrochemiluminescence assay negative molecules (IA+/ECLA−), and enriched for high affinity analyte molecules; or
      (iii) immunoassay positive and electrochemiluminescence as say negative molecules (IA+/ECLA−), and enriched for analyte molecules that bind the target molecule at a binding site not recognized by electrochemiluminescence assay (ECLA); and
   (f) confirming specific binding affinity of an analyte molecule selected from the enriched pool of candidate analyte molecules.

2. The method of claim 1, wherein the pool of candidate molecules is immunoassay negative and electrochemiluminescence assay positive (IA−/ECLA+), and enriched for low affinity analyte molecules.

3. The method of claim 1, wherein the pool of candidate analyte molecules is immunoassay positive and electrochemiluminescence assay positive (IA+/ECLA+) or immunoassay positive and electrochemiluminescence assay negative (IA+/ECLA−), and enriched for high affinity analyte molecules.

4. The method of claim 2, wherein the pool of candidate analyte molecules is immunoassay positive and electrochemiluminescence assay negative (IA+/ECLA−), and enriched for analyte molecules that bind the target molecule at a binding site not recognized by ECLA.

5. A method of identifying candidate low affinity analyte molecules from a pool of analyte molecules, comprising:
   (a) determining ECLA responses for individual members of the pool of analyte molecules binding a target molecule;
   (b) applying a detection limit to the analysis of the ECLA responses, wherein an ECLA response equal to or greater than the ECLA detection limit identifies an electrochemiluminescence assay positive (ECLA+) analyte molecule and an ECLA response less than the ECLA detection limit identifies an electrochemiluminescence assay negative (ECLA−) analyte molecule;
   (c) determining IA responses for individual members of the pool of analyte molecules binding the target molecule;
   (d) applying a detection limit to the analysis of the IA responses, wherein an IA response equal to or greater than the IA detection limit is immunoassay positive (IA+) and an IA response less than the IA detection limit is immunoassay negative (IA−);
   wherein analyte molecules that are immunoassay negative and electrochemilunilnescence assay positive (IA−/ECLA+); and
   (e) confirming specific binding affinity of an analyte molecule selected from the candidate low affinity molecules are identified as candidate low affinity molecules.

6. The method of claim 5, wherein the IA is ELISA and the ELISA detection limit is 0.5 O.D. at 650 nm.

7. The method of claim 5, wherein the detection limit for the ECLA response is 250 electrochemiluminescence units (ECLU).

8. The method of claim 1, wherein a $K_{dissoc}$ of about $10^{-6}$ 1/sec or less identifies a high affinity analyte molecule.

9. The method of claim 1, wherein a $K_{dissoc}$ greater than about $10^{-6}$ 1/sec identifies a low affinity analyte molecule.

10. The method of claim 1, wherein a $K_{dissoc}$ greater or equal to about $10^{-5}$ 1/sec identifies a low affinity analyte molecule.

11. The method of claim 1, wherein a $K_{dissoc}$ greater or equal to about $10^{-3}$ 1/sec identifies a low affinity analyte molecule.

12. The method of claim 1, wherein a $K_D$ equal to or greater than about $10^{-8}$ M identifies a low affinity analyte molecule.

13. The method of claim 1, wherein a $K_D$ of about $10^{-6}$ M to about $10^{-8}$ M identifies a low affinity analyte molecule.

14. The method of claim 1, wherein the analyte molecules are antibodies or antigen binding portions thereof.

15. The method of claim 14, wherein the antibodies are anti-therapeutic antibodies.

16. The method of claim 1, wherein the target molecule is an antigen.

17. The method of claim 16, wherein the antigen is an antibody or antigen binding portion thereof.

18. The method of claim 1, wherein the target molecule is an antibody or antigen binding fragment thereof.

19. The method of claim 18, wherein the antibody is a therapeutic antibody.

20. The method of claim 19, wherein the antibody binds CD20.

21. The method of claim 19, wherein the antibody binds vascular endothelial growth factor (VEGF).

22. The method of claims 14, wherein the antibodies are monoclonal.

23. The method of claim 14, further comprising isotyping the antibodies.

24. The method of claim 14, wherein the antibodies are IgG.

25. An antibody having a $K_{dissoc}$ in the range of $10^{-2}$ 1/sec to $10^{-6}$ 1/sec prepared by the method of claim 1.

26. An antibody having a $K_D$ in the range of $10^{-6}$ M to $10^{-8}$ M prepared by the method of claim 1.

27. The antibody of claim 25, comprising an anti-therapeutic antibody.

28. The antibody of claim 26, comprising an anti-therapeutic antibody.

* * * * *

UNITED STATES PATENT AND TRADEMARK OFFICE
CERTIFICATE OF CORRECTION

PATENT NO. : 7,514,223 B2 Page 1 of 1
APPLICATION NO. : 11/128981
DATED : April 7, 2009
INVENTOR(S) : Jihong Yang et al.

It is certified that error appears in the above-identified patent and that said Letters Patent is hereby corrected as shown below:

In claim 5, column 28, line 23 through line 28, please replace

"wherein analyte molecules that are immunoassay negative and electrochemiluminescence assay positive ($IA^-/ECLA^+$); and (e) confirming specific binding affinity of an analyte molecule selected from the candidate low affinity molecules are identified as candidate low affinity molecules."

with

-- wherein analyte molecules that are immunoassay negative and electrochemiluminescence assay positive ($IA^-/ECLA^+$) are identified as candidate low affinity molecules; and (e) confirming specific binding affinity of an analyte molecule selected from the candidate low affinity molecules. --

Signed and Sealed this

First Day of September, 2009

David J. Kappos
*Director of the United States Patent and Trademark Office*